(12) United States Patent
Demchenko et al.

(10) Patent No.: US 9,120,838 B2
(45) Date of Patent: Sep. 1, 2015

(54) SACCHARIDE CONJUGATES

(75) Inventors: Alexei Demchenko, Glen Carbon, IL (US); Michael R. Nichols, St. Charles, MO (US); Sophon Kaeothip, Bangkok (TH)

(73) Assignee: Curators of the University of Missouri, Columbia, MO (US)

( * ) Notice: Subject to any disclaimer, the term of this patent is extended or adjusted under 35 U.S.C. 154(b) by 20 days.

(21) Appl. No.: 14/112,830

(22) PCT Filed: Apr. 18, 2012

(86) PCT No.: PCT/US2012/034064
§ 371 (c)(1),
(2), (4) Date: Nov. 11, 2013

(87) PCT Pub. No.: WO2012/145392
PCT Pub. Date: Oct. 26, 2012

(65) Prior Publication Data
US 2014/0066390 A1    Mar. 6, 2014

Related U.S. Application Data

(60) Provisional application No. 61/517,380, filed on Apr. 18, 2011.

(51) Int. Cl.
| | | |
|---|---|---|
| *C07H 15/04* | (2006.01) | |
| *A61K 9/00* | (2006.01) | |
| *A61K 47/06* | (2006.01) | |
| *A61K 47/12* | (2006.01) | |
| *A61K 9/06* | (2006.01) | |
| *A61K 47/32* | (2006.01) | |
| *A61K 47/38* | (2006.01) | |
| *A61K 9/20* | (2006.01) | |
| *A61K 47/02* | (2006.01) | |
| *A61K 47/10* | (2006.01) | |
| *A61K 9/48* | (2006.01) | |

(52) U.S. Cl.
CPC ............... *C07H 15/04* (2013.01); *A61K 9/008* (2013.01); *A61K 9/0014* (2013.01); *A61K 9/0019* (2013.01); *A61K 9/06* (2013.01); *A61K 9/2018* (2013.01); *A61K 9/2054* (2013.01); *A61K 47/06* (2013.01); *A61K 47/12* (2013.01); *A61K 47/32* (2013.01); *A61K 47/38* (2013.01); *A61K 9/2027* (2013.01); *A61K 9/2059* (2013.01); *A61K 9/4858* (2013.01); *A61K 47/02* (2013.01); *A61K 47/10* (2013.01)

(58) Field of Classification Search
None
See application file for complete search history.

(56) References Cited

U.S. PATENT DOCUMENTS

| 7,538,092 B2 | 5/2009 | Orlando et al. |
| 2007/0274989 A1 | 11/2007 | Fung et al. |
| 2008/0233599 A1 | 9/2008 | Marchal et al. |
| 2008/0293620 A1 | 11/2008 | Marchal et al. |
| 2009/0041836 A1 | 2/2009 | Boons et al. |
| 2010/0009902 A1 | 1/2010 | Defrees |

OTHER PUBLICATIONS

Wang, Shock, vol. 20, No. 5, pp. 402-414, 2003.*
Boer et al., "Design, synthesis, and biological evaluation of $\alpha_4\beta_1$ integrin antagonists based on $\beta$-$_D$-Mannose as rigid scaffold," Agnew. Chem. (2001) 113 (20) 3989.
Bretthauer et al., "Synthesis of the Mannosyl-*O*-Serine (Threonine) linkage of glycoproteins from Polyisoprenylphosphate Mannose in yeast (*Hansenula holstii*)," Archives of Biochemistry and Biophysics (1975) 167: 151-160.
Buskas et al., "Glycopeptides as versatile tools for glycobiology," Glycobiology (2006) 16 (8): 113R-136R.
Csonka et al., "Ab initio conformational space study for model compounds of O-Glycosides of serine diamide," Chem. Eur. J. (2002) 8 (20): 4718-4733.
Filira et al., "Synthesis of *O*-glycosylated tuftsins by utilizing threonine derivatives containing an unprotected monosaccharide moiety," International Journal of Peptide and Protein Research (Jul. 1990) 36 (1): 86-96.
Hodosi et al., "Manipulation of free carbohydrates via stannylene acetals. Preparation of β-per-*O*-acyl derivatives of $_D$-mannose, $_L$-rhamnose, 6-*O*-trityl-$_D$-talose, and $_D$-lyxose," Carbohydrate Research (1997) 303: 239-243.
Marron et al., "C-Mannose derivatives as potent mimics of Sialyl Lewis X," Tetrahedron Letters (1996) 37 (50): 9037-9040.
Kaeothip et al., "Development of LPS antagonistic therapeutics: synthesis and evaluation of glucopyroanoside-spacer-amno acid motifs," RSC Advances (2011) 1: 83-92.
Shimizu et al., "Biological activities of chemically synthesized *N*-acetylneuraminic acid-($\alpha$2→6)—monosaccharide analogs of lipid A," FEBS Letters (Feb. 1988) 228 (1): 99-101.
International Search Report for corresponding International Application No. PCT/US2012/034064 mailed on Oct. 4, 2012.
Written Opinion for corresponding International Application No. PCT/US2012/034064 mailed on Oct. 4, 2012.

* cited by examiner

*Primary Examiner* — Layla Bland
(74) *Attorney, Agent, or Firm* — Haukaas Fish PLLC; Michael H. Haukaas

(57) ABSTRACT

The invention provides a series of novel Lipid A analogs that are structually simple, synthetically accessible, and capable of blocking the cellular receptor within the signal transduction pathway. The novel Lipid A analogs can include a monosaccharide core with hydrophobic side chains and amino acid ionic motif. The invention further provides methods of using the compounds and compositions thereof in various therapeutic methods.

19 Claims, 4 Drawing Sheets

SACCHARIDE CONJUGATES

RELATED APPLICATIONS

This application is a National Stage Application of PCT/US2012/034064, filed on Apr. 18, 2012, which claims priority to U.S. Provisional Patent Application No. 61/517,380, filed Apr. 18, 2011, and which applications are incorporated herein by reference.

GOVERNMENT SUPPORT

This invention was made with government support under Grant No. 1R15AG033913-01 awarded by the National Institutes of Health. The United States Government has certain rights in the invention.

BACKGROUND OF THE INVENTION

Septicemia is a serious world-wide health problem associated with mortality rates of 40-60%. It has been estimated that 1% of hospital patients and 20-30% of ICU patients develop sepsis. The cardiovascular consequences of septic shock resulting from bacterial infections include myocardial dysfunction that develops in nearly all patients, vascular tone and permeability abnormalities, as well as abnormal oxygen delivery and metabolism. As a result, vital organs such as the brain, heart, kidneys, and liver may be affected or may fail, and this reflects in over 100 000 deaths annually in the US. Septic shock is initiated by the introduction of a bacterial endotoxin (or lipopolysaccharide, LPS) into the blood stream. LPS (FIG. 1), a vital component of the outer leaflet of the gram-negative outer membrane, has been shown to be a principle mediator of the depression of left ventricular function and myocardial contractility.

LPS is comprised of three structural regions. One of these, the Lipid A region, consists of a polyacylated glucosamine disaccharide and is largely responsible for the toxic activity. The results of recent studies suggest that the ensuing proinflammatory response to LPS is by far more dangerous than the mere presence of LPS in circulation. LPS exerts its effects via interaction with a plasma LPS-binding protein (LBP), which has strong affinity for both the Lipid A region of the endotoxin and glycosylphosphatidyl inositol-anchored LPS receptor CD14 on mononuclear phagocytes. The LPS-LBP complex then interacts with CD14 followed by further complex formation with Toll-like receptor 4 (TLR4) and its co-receptor MD-2. TLR4 is an integral membrane protein that transmits the LPS signal to the inside of the cell and initiates the signaling pathways that lead to production of proinflammatory molecules, such as the cytokine, tumor necrosis factor α (TNFα).

Recent advances in the understanding of LPS structure-function relationships have provided some clues on the structural determinants responsible for the endotoxic activity of Lipid A. These determinants include the number and chain length of fatty acids (lipids), the disaccharide core, and the 1,4'-diphosphate groups of the *E. coli* type (1, FIG. 1). The fair stability (chemical or in vitro) of this class of compounds has been a major drawback in their synthesis and application. Although the exact role of the phosphate moieties is still unknown, the observation that a 1-hydroxyl-4'-O-phosphate derivative was inactive gave rise to a belief that the omission of at least one phosphate results in a complete loss of activity (Rossignol et al., *Endotoxin in Health and Disease*, eds. Brade, Opal, Vogel and Morrison, Marcel Dekker, Inc., New York—Basel, 1999, pp. 699-717; Christ et al., *J. Am. Chem. Soc.*, 1994, 116, 3637-3634).

Accordingly, there is a need for compounds that antagonize LPS signaling without activating the inflammatory cascade. There is also a need for Lipid A analogs that lack the complexity of the highly lipidated diphosphorylated disaccharide core yet still maintain potent antagonistic activity against LPS.

SUMMARY

The invention provides compounds, such as lipopolysaccharide antagonists, that can have various biological and medical applications. For example, a new and structurally simplified series of Lipid A analogs is described. The Lipid A analogs can be carbohydrate conjugate and can include a carboxyl moiety and highly lipophilic chains. The inventive lipid A analogs, such as the monosaccharide-amino acid conjugates, can include a monosaccharide core with hydrophobic side chains and amino acid ionic motif.

Accordingly, the invention provides a compound of Formula I:

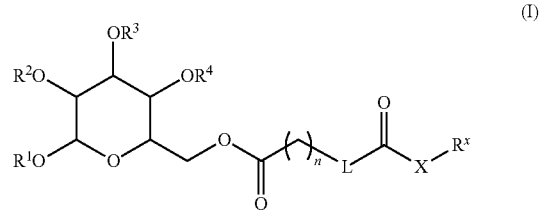

(I)

wherein $R^1$ is $(C_1-C_6)$alkyl;

$R^2$ and $R^3$ are each independently $(C_8-C_{24})$alkyl; $(C_8-C_{24})$alkenyl; or $(C_8-C_{24})$alkanoyl;

$R^4$ is H, $(C_1-C_6)$alkyl, or aryl;

n is 0-9;

L is a methylene, a linking group or a direct bond;

X is O, S, or N;

$R^x$ is an oxygen-linked, sulfur-linked, or nitrogen-linked amino acid that is optionally protected on oxygen or nitrogen with an oxygen or nitrogen protecting group, or that is optionally substituted on a nitrogen of the amino acid with one, two, or three alkyl groups (e.g., thereby forming an alkylated amino group or a quaternary ammonium group on the nitrogen);

wherein any alkyl, alkenyl, alkanoyl or aryl is optionally substituted with one or more substituents, such as hydroxy, oxo, alkyl, alkoxy, alkylcarbonyl, alkylcarbonyloxy, nitro, halo, trifluoromethyl, trifluoromethoxy, cyano, or amino groups, or a combination thereof;

or a pharmaceutically acceptable salt or solvate thereof.

The invention also provides compounds of Formula II:

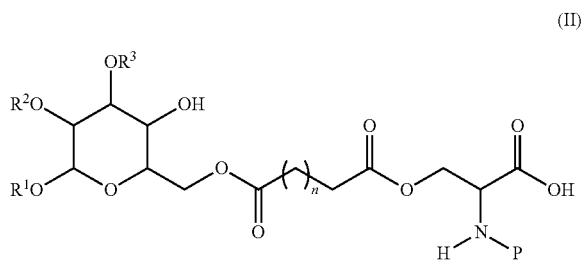

(II)

wherein n is 0, 1, 2, or 3; P is a nitrogen protecting group; or a pharmaceutically acceptable salt or solvate thereof, where the remaining variables are as defined for Formula I. The amino group of Formula II (the —N(H)(P) group) can also be alkylated to form a dialkyl amine, or a trialkyl ammonium group, which can then include any pharmaceutically acceptable counterion.

The invention also provides compounds of Formula III:

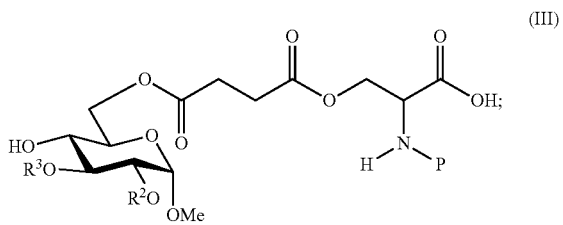

(III)

or a pharmaceutically acceptable salt or solvate thereof, wherein $R^2$, $R^3$, and P are as defined for Formula II. The amino group of Formula III (the —N(H)(P) group) can also be alkylated to form a dialkyl amine, or a trialkyl ammonium group, which can then include any pharmaceutically acceptable counterion.

Any of the compounds described herein can be combined with a a pharmaceutical carrier, diluent, or excipient to provide a pharmaceutical composition. The composition can be formulated, for example, for intraperitoneal injection or infusion to a mammal.

The invention also provides methods for treating or inhibiting the deleterious effects of endotoxemia or septic shock. The methods can include administering to a subject afflicted with endotoxemia or septic shock an effective amount of a compound or composition described herein wherein the deleterious effects of endotoxemia are thereby treated or inhibited. The deleterious effects of endotoxemia or septic shock can be one or more of a reduction in white blood cells, a high respiratory rate, an elevated heart rate, an elevated temperature, or multiple organ failure.

The invention further provides methods for blocking or inhibiting the signal transduction pathway that leads to sepsis. The method can include administering to a subject afflicted with, or having an increased risk of being afflicted with, sepsis, an effective amount of a compound or composition described herein wherein the signal transduction pathway that leads to sepsis is blocked or inhibited.

The invention also provides compounds that block a cellular receptor within a signal transduction pathway. The methods can include using the compounds to block the signal transduction pathway that leads to sepsis.

The invention also provides novel compounds of the formulas described herein, intermediates for the synthesis of compounds of the formulas described herein, as well as methods of preparing compounds of the formulas described herein. The invention also provides compounds of the formulas described herein that are useful as intermediates for the synthesis of other useful compounds. The invention provides for the use of compounds of F the formulas described herein for the manufacture of medicaments useful for the treatment of inflammation and/or bacterial infections in a mammal, such as a human.

The invention yet further provides for the use of the compounds and compositions described herein for use in medical therapy. The medical therapy can be treating inflammation, sepsis, or endotoxemia. The invention also provides for the use of a composition as described herein for the manufacture of a medicament to treat the aforementioned conditions. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Sepsis is a serious medical condition characterized by bacterial infection and a subsequent massive systemic inflammatory response. The release of proinflammatory products and mediators from responding innate immune cells, such as mononuclear phagocytes, directly contributes to the pathogenesis of sepsis. The primary bacterial trigger of inflammation is lipopolysaccharide (LPS), which interacts with the germline-encoded macrophage receptor cluster of differentiation 14 (CD14) via its Lipid A moiety. In an effort to identify compounds that block LPS-induced inflammation, a series of Lipid A analogs that lack a disaccharide core yet still possess potent antagonistic activity against LPS were investigated. Compounds containing the following moieties were developed: a glucopyranoside core, hydrophobic ether substituents, and an amino acid to provide an ionic character to the constructs. An efficient synthesis of these compounds and the ensuing biological studies thereof are described herein.

To develop molecules that antagonize LPS signaling without activating the inflammatory cascade, simplified Lipid A analogs that lack the complexity of the highly lipidated diphosphorylated disaccharide core yet still maintain potent antagonistic activity against LPS were developed. The synthesis, and unprecedented LPS-antagonistic activity, of various methyl glucopyranoside-amino acid conjugates is described below. This project was inspired by published reports of compounds that are structurally dissimilar to Lipid A yet still exhibit potent antagonistic activity. Amongst a myriad of research articles that have been disseminated in the past years, the following three noteworthy discoveries provided background for the new developments.

Figure 1:
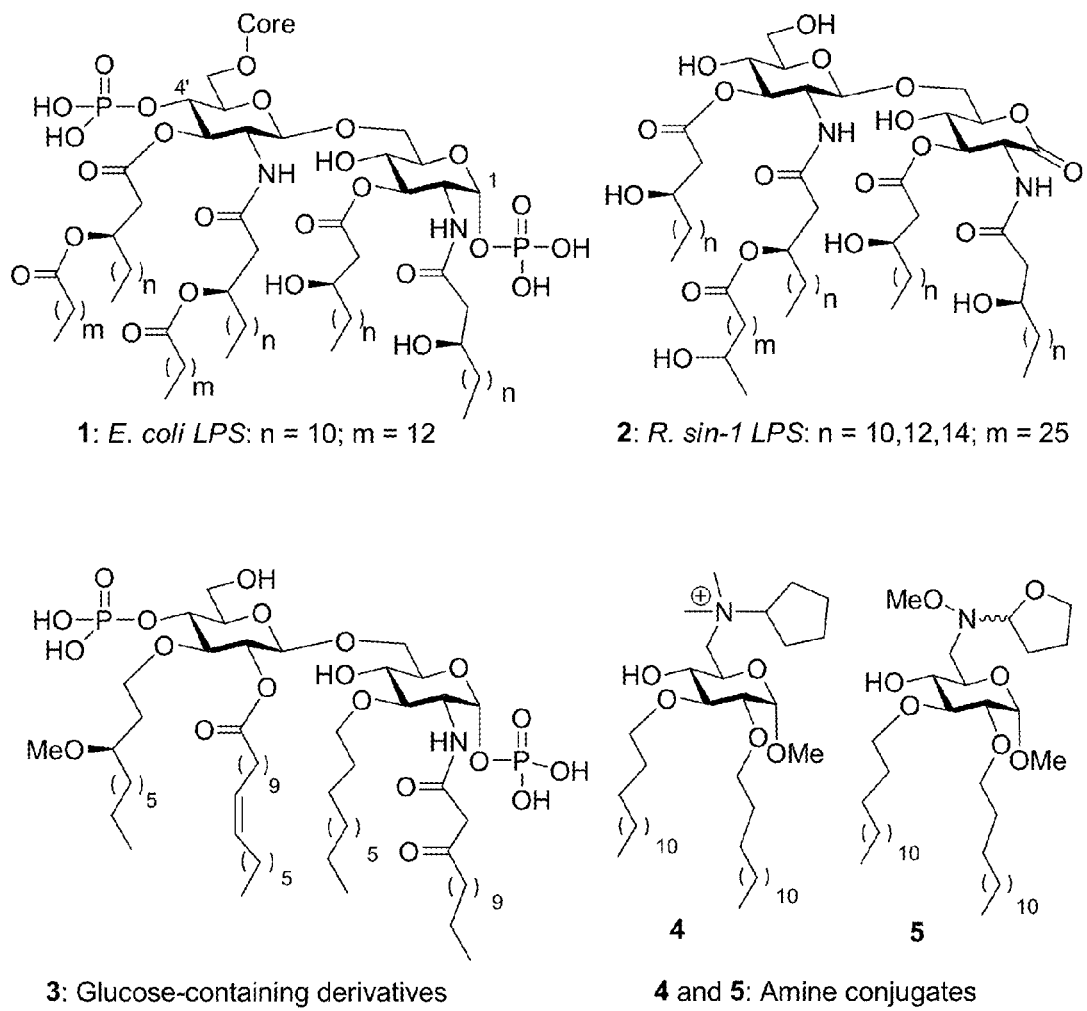
FIG. 1. Structures of the Lipid A region of *E. coli* LPS (1) and known structural mimetics thereof (2-5). Compound 2 was reported by Boons et al. (*J. Am. Chem. Soc.*, 2003, 125, 6103-6112). Compound 3 was reported by Shiozaki et al. (*Tetrahedron*, 2006, 62, 205-225). Compounds 4 and 5 were reported by Peri et al. (*Angew. Chem., Int. Ed.*, 2007, 46, 3308-3312).

First, as reported by Boons et al. (*J. Am. Chem. Soc.*, 2003, 125, 6103-6112), a strong binding and antagonistic effect was achieved even with 'phosphateless' *Rhizobium* syn-1 disaccharide 2, which bears a lactone moiety at the reducing end (FIG. 1). Second, Shiozaki et al. (*Tetrahedron*, 2006, 62, 205-225) showed that a strong anti-LPS antagonistic response can be achieved, even with disaccharide 3, in which the non-reducing glucosamine is replaced with glucose. Third, Pen et al. (*Angew. Chem., Int. Ed.*, 2007, 46, 3308-3312) demonstrated that methyl glycoside-heterocycle conjugates 4 and 5 provide antagonistic activity. In view of these structural dissimilarities from *E. coli* LPS, the development molecules that contain the new structural variations, while maintaining antagonistic activity, was sought. It was surprisingly found that compounds that included various moieties such as a methyl glucoside monosaccharide core, one or more hydrophobic chains to facilitate membrane intercalation, and an amino acid to provide an ionic character, were able to provide potent antagonistic activity. An efficient synthesis of conjugates of this type, and biological studies of their endotoxic activity in vitro, is described herein.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Ed., by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

Specific values listed below for radicals, substituents, and ranges, are for illustration only; they do not exclude other defined values or other values within defined ranges for radicals and substituents. Generic terms include each of their species, and in other embodiments, can exclude one or more of their species. For example, the term halo includes and can explicitly be fluoro, chloro, bromo, or iodo.

The term "alkyl" refers to a branched, unbranched, or cyclic hydrocarbon having, for example, from 1-30 carbon atoms, and often 1-12, 1-10, 1-8, 1-6, or 1-4 carbon atoms. Examples include, but are not limited to, methyl, ethyl, 1-propyl, 2-propyl(iso-propyl), 1-butyl, 2-methyl-1-propyl(isobutyl), 2-butyl(sec-butyl), 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, tetradecyl, octadecyl, and the like. The alkyl can be unsubstituted or optionally substituted, for example, with one or more substituents described below. In some embodiments, the alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

For example, the alkyl group can be substituted with one or more alkyl group substituents that can be the same or different, where the "alkyl group substituent" can be an alkyl, halo, arylamino, acyl, hydroxyl, aryloxy, alkoxyl, alkylthio, arylthio, aralkyloxy, aralkylthio, carboxy, alkoxycarbonyl, oxo or cycloalkyl. There can be optionally inserted along the alkyl chain one or more oxygen, sulfur or substituted nitrogen atoms, wherein the nitrogen substituent is hydrogen, lower alkyl (thereby forming an "alkylaminoalkyl"), or aryl. "Branched" alkyl groups can be an alkyl group in which a lower alkyl group, such as methyl, ethyl or propyl, is attached to linear alkyl chain.

The term "alkenyl" refers to a partially unsaturated alkyl group (i.e. an alkyl that includes at least one carbon-carbon, $sp^2$ double bond) having about 2 to about 30 carbon atoms in a chain. In some embodiments, the alkenyl group can include 2 to about 24 carbon atoms, 2 to 10 carbon atoms, 2 to 6 carbon atoms, or 2 to 4 carbon atoms. Examples include, but are not limited to, ethylene or vinyl, allyl, cyclopentenyl, and 5-hexenyl. The alkenyl can be unsubstituted or substituted, for example, by one or more alkyl groups or other substituents described below. The alkenyl can be a substituent (monoradical) or an internal group (an alkenylene). The alkenyl group can be straight, branched or cyclic. The alkenyl group can be also optionally unsaturated and/or substituted with one or more "alkyl group substituents". There can be optionally inserted along the alkenyl group one or more oxygen, sulfur or substituted nitrogen atoms, wherein the nitrogen substituent is alkyl as previously described.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl group can be monovalent or divalent, and can be optionally substituted, for example, by one or more alkyl groups or other substituents described below. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like. There can be optionally inserted along the cyclic alkyl chain one or more oxygen, sulfur or substituted nitrogen atoms, wherein the nitrogen substituent is hydrogen, lower alkyl, or aryl, thus providing a heterocyclic group.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups. The aromatic rings of the aryl group may each and optionally contain heteroatoms. The aryl group can be optionally substituted with one or more aryl group substituents that can be the same or different, where "aryl group substituent" can include an alkyl, aryl, arylalkyl (e.g., benzyl), hydroxy, alkoxyl, aryloxy, arylalkoxyl, carboxy, acyl, halo, nitro, alkoxycarbonyl, aryloxycarbonyl, arylalkoxycarbonyl, acyloxy, acylamino, aroylamino, carbamoyl, alkylcarbamoyl, dialkylcarbamoyl, arylthio, alkylthio, alkenyl or —NRR' group, where R and R' can each independently be hydrogen, alkyl, aryl or arylalkyl.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, or cyano. Additionally, suitable substituent groups can be, for example, —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

The term "residue" refers to an atom or group of atoms that are part of a larger molecule. For example, while an amino acid is a compound, one can refer to an amino acid residue as the compound linked to another molecule through a covalent bond, such as by the formal removal of a hydrogen from an amino terminus, a carboxy terminus, or from a side chain of the amino acid, to form a direct bond with the other molecule. A residue can also refer to a portion of a molecule used to link one molecule to another molecule to form a conjugate. Typical residues of an amino acid include its amino residue and its carboxylic acid residue. Appropriate residues can often be condensed to form linkages. For example, an amino residue and a carboxylic acid residue can be condensed to form a peptide bond. A typical residue of a saccharide includes any one of its hydroxyl groups, and in several embodiments, the anomeric hydroxyl.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "endotoxemia" refers to a blood condition where endotoxins are present in the blood, leading to inflammation. When the endotoxins are derived from gram-negative (and/or rod-shaped) bacteria, their presence can cause hemorrhages, necrosis of the kidneys, and septic shock.

The term "septic shock" refers to a condition resulting from severe infection and sepsis, where the infection can be local or systemic. In humans, septic shock has a specific definition requiring several conditions to be met for diagnosis. First, SIRS (systemic inflammatory response syndrome) must be diagnosed by finding at least any two of the following: a) tachypnea (high respiratory rate) >20 breaths per minute, or on blood gas, a PCO$_2$ less than 32 mmHg signifying hyperventilation; b) white blood cell count either significantly low, <4000 cells/mm$^3$ or elevated >12000 cells/mm$^3$; c) heart rate >90 beats per minute; and d) high temperature: fever >38.5° C. (101.3° F.) or hypothermia <35.0° C. (95.0° F.). Second, there must be sepsis. Sepsis requires evidence of infection, which may include positive blood culture, signs of pneumonia on chest x-ray, or other radiologic or laboratory evidence of infection. Third, signs of end-organ dysfunction are required such as renal failure, liver dysfunction, changes in mental status, or elevated serum lactate. Finally, septic shock is diagnosed if there is refractory hypotension (low blood pressure that does not respond to treatment). This signifies that intravenous fluid administration alone is insufficient to maintain a patient's blood pressure from becoming hypotensive.

Septic shock resulting from gram-negative bacterial infections is initiated by movement of bacterial endotoxin (LPS) into the blood stream. LPS is a vital component of the outer leaflet of the gram-negative outer membrane. It is comprised of three structural units, among which a Lipid-A region consisting of a polyacylated glucosamine disaccharide is largely responsible for the toxic activity of LPS. Evidence of a proinflammatory response to LPS is more important than detection of LPS in circulation. The effects of LPS are initiated after it interacts with a plasma LPS-binding protein (LPB). LPB has a strong affinity for the Lipid-A portion of endotoxin, as well as or glycophosphatidyl inositol-anchored LPS receptor CD14 on mononuclear phagocytes. When a LPS-LPB complex interacts with CD14 (and then TLR-4), the cells produce a variety of proinflammatory factors, such as TNFα. The compounds described herein can inhibit the production of such proinflammatory factors.

Protecting Groups

The term "protecting group" refers to any group that, when bound to a hydroxyl, nitrogen, or other heteroatom, prevents undesired reactions from occurring at the sight of the heteroatom, and which group can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, Chapter 5, Carbonyl Protecting Groups, pages 155-184, and Chapter 7, Protection for the Amino Group. See also Kocienski, Philip J.; *Protecting Groups* (Georg Thieme Verlag Stuttgart, New York, 1994), which is incorporated herein by reference in its entirety, and D. Voet, *Biochemistry*, Wiley: New York, 1990; L. Stryer, *Biochemistry*, (3rd Ed.), W. H. Freeman and Co.: New York, 1975; and J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein, for various protecting group manipulations and other synthetic transformations.

Specific useful protecting groups include benzyl, acetyl, trifluoroacetyl, benzoyl, benzyloxycarbonyl, Fmoc, and silicon protecting groups such as trimethylsilyl, t-butyldimethylsilyl, and diphenylmethylsilyl. Some specific protecting groups that can be employed in conjunction with the methods of the invention are discussed below.

Typical nitrogen protecting groups described in Greene (pages 14-118) include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate(tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); and sulfonates (sulfate, methanesulfonate (mesylate), benzylsulfonate, tosylate, triflate).

Isomers

As to any of compound described herein, which contains one or more substituents, it is understood, of course, that such groups do not contain any substitution or substitution patterns that are sterically impractical and/or synthetically non-feasible. The total molecular weight of substituents on a single group will typically be less than about 600, 500, 400, 300, 200, or 100. It will be appreciated that the compounds of the invention can contain asymmetrically substituted carbon atoms, and may be isolated in optically active or racemic forms. It is well known in the art how to prepare optically active forms, such as by resolution of racemic forms or by synthesis from optically active starting materials or by the use of enantioselective catalytic reactions. All chiral, diastereomeric, racemic forms and all geometric isomeric forms of a compound are intended as part of this invention.

Throughout the specification and claims, a given chemical formula or name not having a specific designation shall encompass all optical and stereoisomers as well as racemic mixtures where such isomers and mixtures exist.

One diastereomer may display superior activity compared to another. When required, separation of racemic materials can be achieved by high performance liquid chromatography (HPLC) using a chiral column or by a resolution using a resolving agent such as camphonic chloride, as in Thomas J. Tucker et al., *J. Med. Chem.* 1994, 37, 2437-2444. A chiral compound may also be directly synthesized using a chiral catalyst or a chiral ligand; see, for example, Mark A. Huffman et al., *J. Org. Chem.* 1995, 60, 1590-1594.

COMPOUNDS OF THE INVENTION

A compound of Formula I:

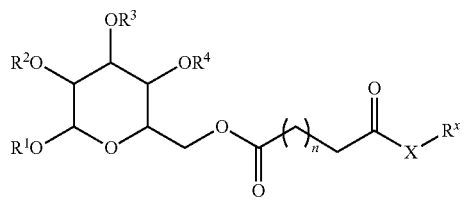

(I)

wherein $R^1$ is $(C_1-C_6)$alkyl;

$R^2$ and $R^3$ are each independently $(C_8-C_{24})$alkyl; $(C_8-C_{24})$alkenyl; or $(C_8-C_{24})$alkanoyl, optionally substituted or interrupted, including where the alkyl, alkenyl, or alkanoyl is one of various fatty acid moieties;

$R^4$ is H, $(C_1-C_6)$alkyl, or aryl;

n is 0-9;

L is a methylene, a linking group or a direct bond;

X is O, S, or N;

$R^x$ is an oxygen-linked, sulfur-linked, or nitrogen-linked amino acid that is optionally protected on oxygen or nitrogen with an oxygen or nitrogen protecting group;

wherein any alkyl, alkenyl, alkanoyl or aryl is optionally substituted with one or more hydroxy, oxo, alkyl, alkoxy, alkylcarbonyl, alkylcarbonyloxy, nitro, halo, trifluoromethyl, trifluoromethoxy, cyano, or amino groups;

or a pharmaceutically acceptable salt or solvate thereof.

Specific values for $R^1$ include methyl, ethyl, and propyl.

Specific values for $R^2$ and $R^3$ include any one or more of the saccharide fatty acid substituents described or illustrated herein.

The linker L can be a methylene, a direct bond, or a divalent radical "linking group" of the formula —W-A-W— wherein W is —N(R')C(=O)—, —C(=O)N(R')—, —OC(=O)—, —C(=O)O—, —O—, —S—, —S(O)—, —S(O)$_2$—, —N(R')—, —C(=O)—, or absent; wherein each R' is independently H, $(C_1-C_6)$alkyl, or a nitrogen protecting group; and A can be $(C_1-C_{20})$alkyl, $(C_2-C_{16})$alkenyl, $(C_2-C_{16})$alkynyl, $(C_3-C_8)$cycloalkyl, $(C_6-C_{10})$aryl, —(OCH$_2$—CH$_2$)$_n$— where n is 1 to about 20, —C(O)NH(CH$_2$)$_n$ wherein n is 1 to about 6, —OP(O)(OH)O—, —OP(O)(OH)O(CH$_2$)$_n$ wherein n is 1 to about 6, —OP(O)(OH)OCH$_2$CH(OH)CH$_2$—, —N$^+$(Me)$_2$(CH$_2$)$_n$— wherein n is 1 to about 6, or $(C_1-C_{20})$alkyl, $(C_2-C_{16})$alkenyl, $(C_2-C_{16})$alkynyl, or —(OCH$_2$—CH$_2$)$_n$— interrupted between two carbons with one, two, or three $(C_3-C_8)$cycloalkyl, heterocycle, or $(C_6-C_{10})$aryl groups; and W (and/or A if one or both W groups is absent) is linked to the corresponding location of Formula I.

The pyranyl group of Formula I can be any monosaccharide moiety. Typical monosaccharides include allose, altrose, glucose, mannose, gulose, idose, galactose, or talose. Other suitable monosaccharides include glucuronic acid, sorbase, ribose, and the like. A saccharide can include hydroxyl protecting groups such as, but not limited to, acetyl groups, benzyl groups, benzylidene groups, silyl groups, methoxy ether groups, or combinations thereof. The saccharide groups can also be in pyranose form, furanose form, or linear form. Depending on the context, as would be understood by one of skill in the art, the saccharide can include the oxygen that links it to another group, or exclude the oxygen that links it to another group.

The saccharide side chains $R^2$ and $R^3$ can be a variety of medium to long-chain alkyl, alkenyl, or alkanoyl groups. As such, the $R^2$ and $R^3$ groups can each independently be fatty acid moieties (e.g., linked to the formula through the oxygen on the $R^2$ or $R^3$ group, wherein the fatty acid moiety refers to the carboxyl group of the fatty acid which is bonded to the oxygen on the $R^2$ or $R^3$ group). The fatty acid moiety can be saturated, monounsaturated, or polyunsaturated, and can be branched or unbranched. The fatty acid moiety can include varying carbon chain lengths ranging from about $C_8$ to $C_{24}$. Common fatty acid moieties include saturated fatty acids such as lauric acid (dodecanoic acid), myristic acid (tetradecanoic acid), palmitic acid (hexadecanoic acid), steric acid (octadecanoic acid), arachidic acid (eicosanoic acid), and lignoceric acid (tetracosanoic acid); unsaturated acids such as palmitoleic (a C16 acid), and oleic acid (a C18 acid); polyunsaturated acids such as linoleic acid (a di-unsaturated C18 acid), linolenic acid (a tri-unsaturated C18 acid), and arachidonic acid (a tetra-unsubstituted C20 acid). The carbon chain of the $R^2$ or $R^3$ group can also be, for example, optionally epoxidized, optionally substituted with one or more hydroxyl groups, optionally substituted with one or more oxo groups, optionally interrupted by one or more oxygen atoms (thereby forming ether or ester groups), or a combination thereof.

Other fatty acid chains can be prepared by standard starting materials and reaction conditions such as those described by Kunau (*Synthesis of unsaturated fatty acids, Chem. Phys. Lipids* 1973, 11, 254-269), Rembold et al. (*Synthesis of Kdo-α-glycosides of lipid A derivatives, Carbohydr. Res.* 1993, 246, 137-159), and Dixon et al. (*The total synthesis of the anonaceous acetogenin, muricatetrocin C, Angew. Chem. Int. Ed.* 2000, 39, 3622-3626). In certain embodiments, one of $R^2$ and $R^3$ can be H.

The $R^x$ group of Formula I is an amino acid residue. The term "amino acid" refers to a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as an unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; tert-butylglycine; and 2,5-diaminohexanedioic acid) residue having one or more open valences. The term also comprises natural and unnatural amino acids bearing nitrogen protecting groups (e.g. acetyl, acyl, trifluoroacetyl, benzyloxycarbonyl, for Fmoc), as well as natural and unnatural amino acids protected at carboxy with oxygen protecting groups (e.g. as a $(C_1-C_6)$alkyl, phenyl or benzyl ester or amide).

In some embodiments, X is oxygen and $R^x$ is oxygen-linked serine, threonine, or tyrosine. In other embodiments, X is sulfur and $R^x$ is sulfur-linked cysteine. The amino group of the serine, threonine, tyrosine, or cysteine can be protected with a nitrogen protecting group, such as an acyl, alkyl, or carbamate group.

The invention also provides compounds where the compound of Formula I is a compound of Formula II:

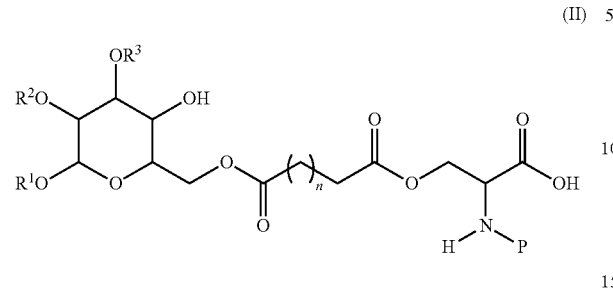

(II)

wherein n is 0, 1, 2, or 3; and P is a nitrogen protecting group; or a pharmaceutically acceptable salt or solvate thereof. In some embodiments, P can bed an Fmoc group.

The invention further provides compounds where the compound of Formula II is a compound of Formula III:

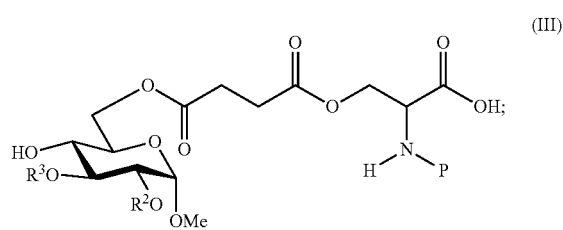

(III)

or a pharmaceutically acceptable salt or solvate thereof.

The groups $R^2$ and $R^3$ can be, for example, $(C_{10}-C_{18})$alkyl, $(C_{10}-C_{18})$alkenyl, or $(C_{10}-C_{18})$alkanoyl groups, optionally substituted on carbon with one or more substituents as described above for the definition of substituent. In certain specific embodiments, $R^2$ and $R^3$ are tetradecanoyl groups, tetradecanyl groups, or a combination thereof.

In one specific embodiment of the invention, the compound is:

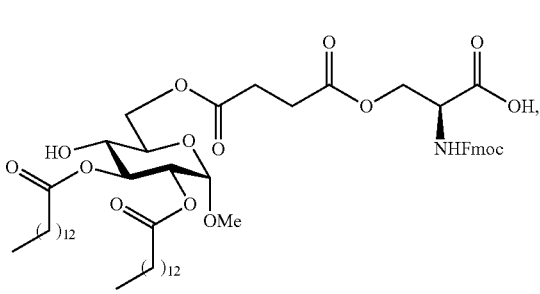

19 or a salt or solvate thereof.

In another specific embodiment of the invention, the compound is:

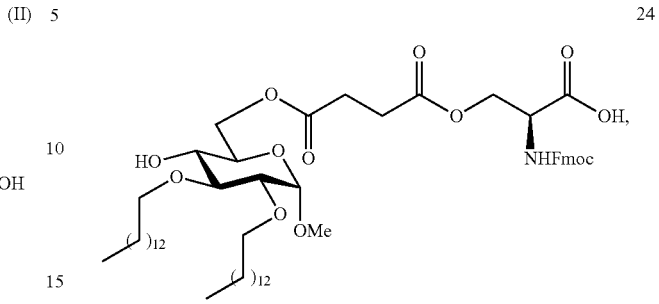

24 or a salt or solvate thereof.

The invention also provides compositions that include a compound described herein and a pharmaceutical carrier, diluent, or excipient. The composition can be formulated, for example, for intraperitoneal injection or infusion to a mammal.

Thus, the invention provides a new class Lipid A analogues with structurally simplified carbohydrate-amino acid conjugates. In some embodiments, the conjugates comprise a monosaccharide code, hydrophobic side chains, and amino acid ionic motif, having Formula IV:

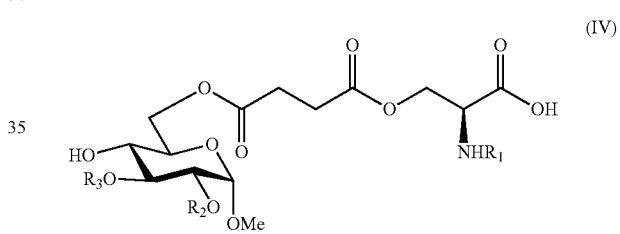

(IV)

where $R^1$ is a nitrogen-protecting group, such as acyl, alkyl, or a carbamate (e.g., Fmoc); and $R^2$ and $R^3$ are each independently alkyl, acyl, alkenyl, aryl, heteroaryl, or cycloalkyl groups. By "independently selected", the skilled artisan will appreciate that each and every group may be selected from the entire list set forth as possible selections without regard to the selections of other groups having the same or different appellations.

Preparation of Conjugates of the Invention.

General Synthetic Methods. Preparation of the compounds described herein can be prepared according to the methods in the Examples below, or may be prepared according to known techniques in the art of organic synthesis. Many saccharides, amino acids, and linking groups are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Additional useful reactions well known to those of skill in the art are referenced in March's *Advanced Organic Chemistry Reactions, Mechanisms, and Structure*, $5^{th}$ Ed. by Michael B. Smith and Jerry March, John Wiley & Sons, Publishers; and Wuts et al. (1999), *Protective Groups in Organic Synthesis*, $3^{rd}$ Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

A variety of monosaccharide-amino acid conjugates were prepared for evaluation. For one set of embodiments, the synthesis began with the conversion of methyl α-D-glucopyranoside 6 into methyl 2,3-di-O-benzyl-α-D-glucopyranoside 7 via sequential 4,6-benzylidene acetal formation, 2,3-dibenzylation, and acetal cleavage accomplished in 67% yield over three steps (Schemes 1 and 2). 4,6-Diol 7 was then regioselectively succinoylated at the primary position with succinic anhydride in the presence of 4-dimethylaminopyridine (DMAP) in pyridine to afford derivative 8 in 71% yield. The carboxyl moiety of the linker was then coupled with 3-hydroxyl of protected L-serine derivative 9. This was accomplished using N,N'-diisopropylcarbodiimide (DIC) as the coupling reagent in the presence of DMAP in pyridine to afford conjugate 10 in 80% yield.

Scheme 1. Synthesis of monosaccharide-amino acid conjugate 10.

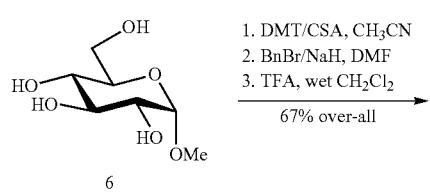

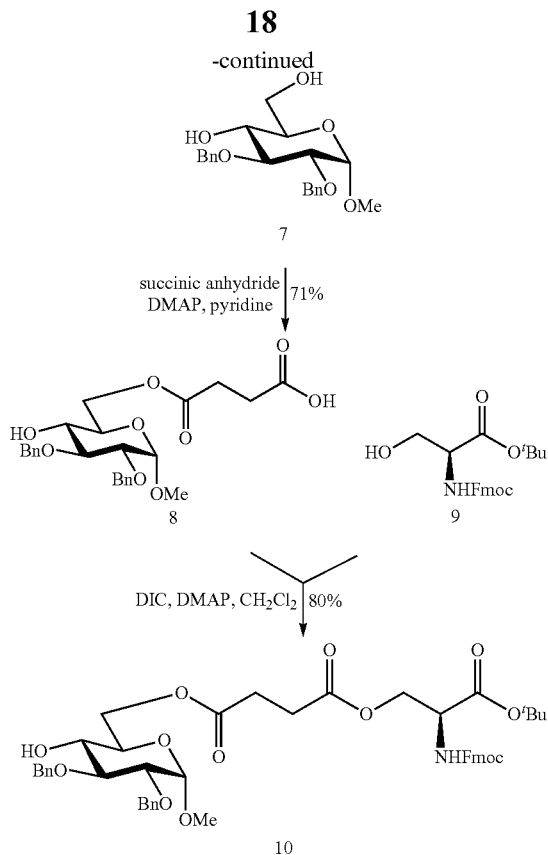

Scheme 2. Synthesis of monosaccharide-amino acid conjugates 11-13.

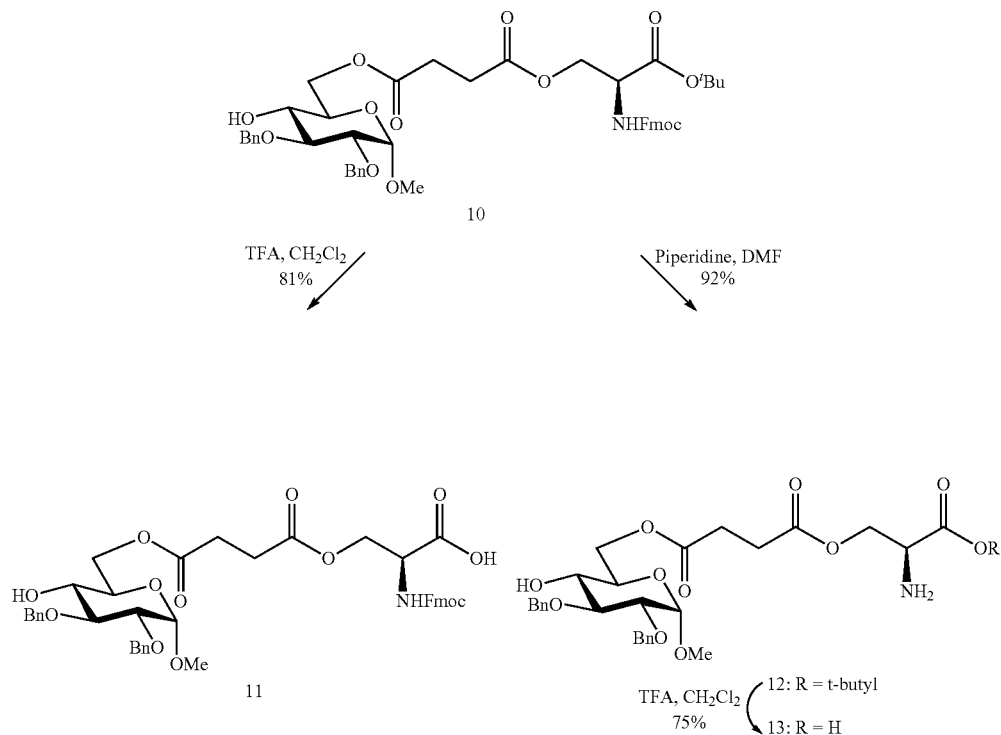

Having obtained a key construct, compound 10, further functional group transformations were pursued. A driving force for these synthetic manipulations was to obtain a series of simple analogs that would allow for investigating the effect of cationic and anionic character on LPS-antagonistic activity in vitro. With this objective in mind, carboxylated compound 11 was obtained from 10 by cleavage of tert-butyl ester in presence of TFA/DCM in 81% yield. Alternatively, the Fmoc protecting group could also be removed from compound 10 with piperidine in DMF to afford free amine 12. Subsequently, compound 13, having both carboxyl and amine groups unprotected, was obtained. This was accomplished by the treatment of compound 12 with TFA/CH$_2$Cl$_2$ to give derivative 13 in 75% yield.

To gain further insight into the effect of various substituents on endotoxic activity of monosaccharide-amino acid conjugates, an analog of compound 11 was obtained in which benzyl groups have been replaced with acyl (myristoyl, C14) fatty acid chains. The synthesis of lipidated analog 19 was accomplished as depicted in Scheme 3.

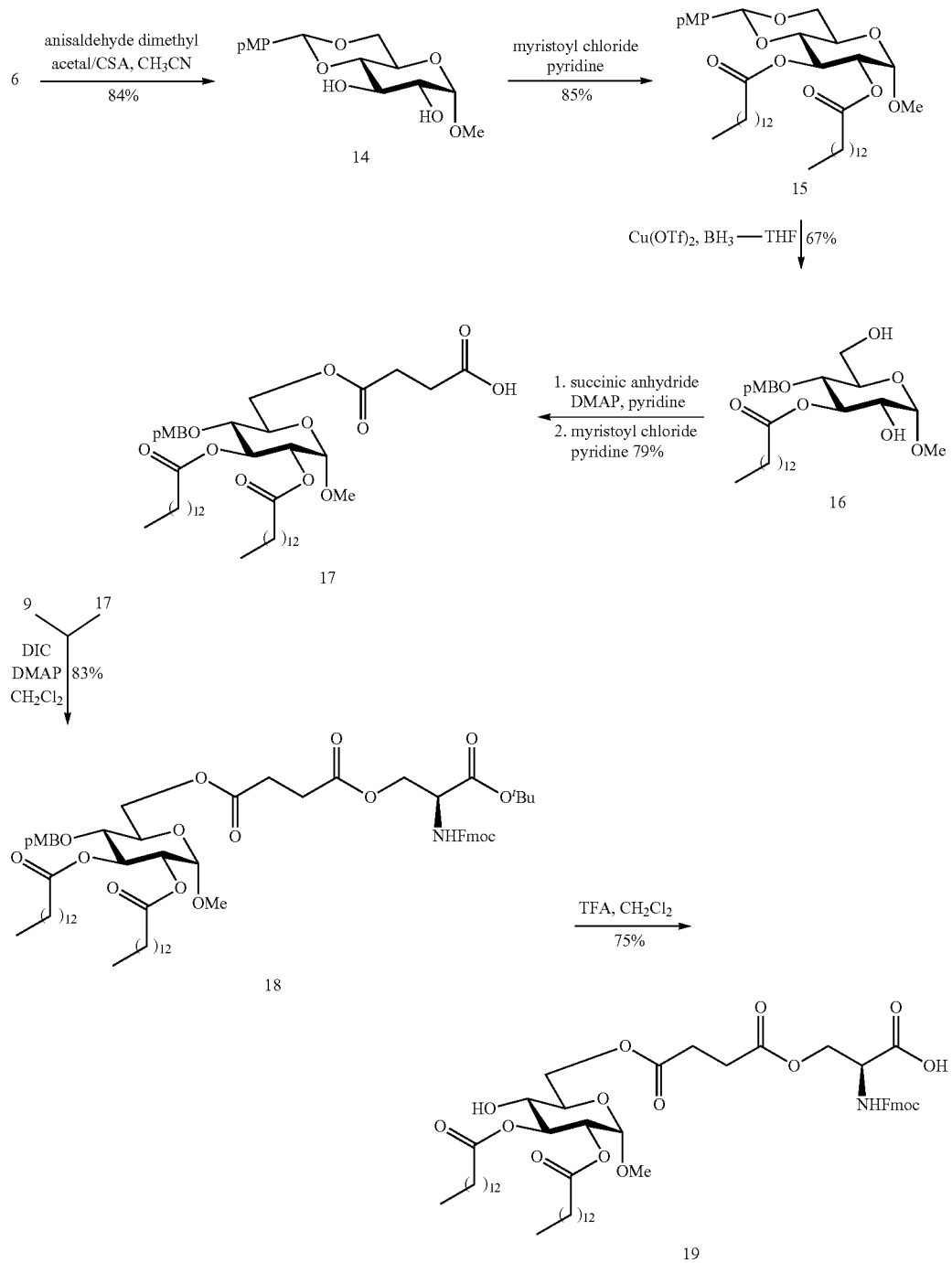

Scheme 3. Preparation of monosaccharide-fatty acid-amino acid conjugate 19.

Methyl glycoside 6 was protected as 4,6-O-(p-methoxy-benzylidene) acetal 14 by treatment with anisaldehyde dimethylacetal in presence of camphorsulfonic acid in 89% yield. The acylation of 14 with myristoyl chloride in the presence of pyridine furnished compound 15 in 85% yield. The benzylidene ring in 15 was reductively opened by treatment with $BH_3$-THF catalyzed with $Cu(OTf)_2$ to obtain unexpected product 16 lacking the C-2 acyl chain in 67% yield. The loss of the acyl chain was rather unexpected, but this glitch was overcome by regioselective acylation with succinic anhydride in pyridine at the primary C-6 position followed by C-2 acylation with myristoyl chloride. This two-step one-pot procedure allowed us to obtain compound 17 in 79% yield.

L-serine derivative 9 was linked to the carboxyl group of 17 of via DIC-mediated coupling in the presence of DMAP. The monosaccharide-fatty acid-amino acid conjugate 18 was obtained in 83% yield. Acid treatment of the fully protected compound 18 led to concomitant cleavage of the p-methoxybenzyl (PMB) group at C-4 and tert-butyl ester. As a result, compound 19 was isolated in 75% yield.

For comparative biological studies, we also accomplished the synthesis of alkylated analog 24 was performed as depicted in Scheme 4. Intermediate 14 was di-alkylated at C-2 and C-3 with myristyl bromide in presence of NaH to afford compound 20 in a 72% yield. The benzylidene ring in 20 was reductively opened by treatment with $BH_3$-THF catalyzed with $Cu(OTf)_2$ to obtain product 22 in 87%. Acylation of 22 with succinic anhydride led to compound 22 in 89% yield. L-serine derivative 9 was then linked to the carboxyl group of 22 via DIC-mediated coupling in the presence of DMAP. The resulting monosaccharide-amino acid conjugate 23 was obtained in 79% yield. Acid treatment of the fully protected compound 23 led to concomitant cleavage of the p-methoxybenzyl (PMB) group at C-4 and tert-butyl ester. As a result, target compound 24 was isolated in 81% yield.

Scheme 4. Synthesis of monosaccharide-alkyl-amino acid conjugate 24.

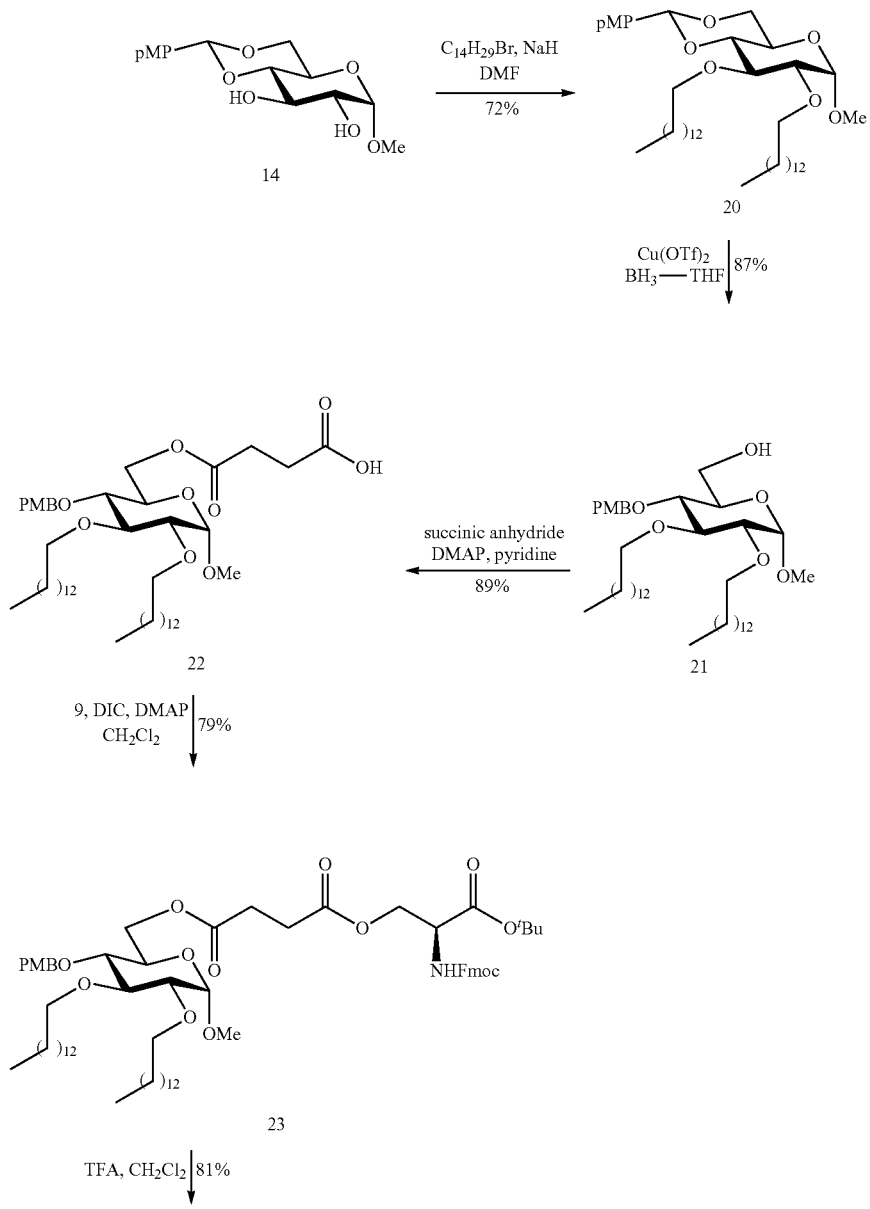

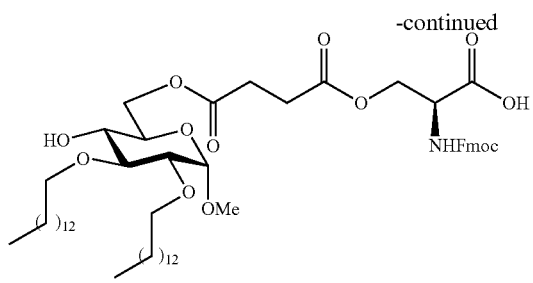

24

Biological Activity. The inhibitory activity of the novel conjugates on LPS-induced TNFα production was investigated in vitro using THP-1 macrophages. THP-1 macrophages are a useful system for studying inflammatory processes and serve as a model for peripheral monocytes/macrophages and their responses to bacterial infection. The cell viability measurements (toxicity) of the novel conjugates were tested using an XTT reduction assay. Table 1 in Example 2 below summarizes the biological data of the conjugates 11, 13, 19, and 24 in comparison to the known Peri conjugate, 4. As shown in Table 1, the potent inhibition displayed by the inventive conjugate 24 of LPS-induced TNFα production without associated toxicity establishes the conjugates as useful therapeutic compounds in preventing the deleterious effects of endotoxemia.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form, often about 0.5 wt. % to about 20 wt. % of a dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a buffer or nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various of the other ingredients enumerated above, as desired, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating endotoxemia in a mammal, which involve administering to a mammal having endotoxemia an effective amount of a compound or composition described herein. A mammal includes a primate, human, rodent, canine, feline, bovine, ovine, equine, swine, caprine, bovine and the like. The ability of a compound of the invention to treat endotoxemia may be determined by using assays well known to the art. For example, the design of treatment protocols, toxicity evaluation, data analysis, quantification of cell kill, and the like are known.

Pharmaceutical formulations that include a compound described herein can also be provided as vaccine adjutants. A vaccine adjuvant can be a therapeutic cancer vaccine adjuvant, such as for the treatment of breast, lung, colon, skin, kidney, prostate, and other cancers. For example, a compound described herein can act as an adjuvant that activates antigen-presenting cells to stimulate immune responses. Additional information and techniques that may be applied to using the compounds described herein as vaccine adjuvants are described by, for example, Buskas et al. (*Immunotherapy for cancer: synthetic carbohydrate-based vaccines; Chem. Commun.* 2009, 5335-5349); and PCT Publication No. WO 2011/156774 (Danishefsky et al.; Multivalent glycopeptide constructs and uses thereof; and U.S. Provisional Application No. 61/353,722, filed Jun. 11, 2010). Accordingly, compounds described herein that stimulate inflammation can be used as vaccine adjuvants.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Chemical Synthesis of Compounds

General

Column chromatography was performed on silica gel 60 (70-230 mesh), reactions were monitored by TLC on Kieselgel 60 F$_{254}$. The compounds were detected by examination under UV light and by charring with 10% sulfuric acid in methanol. Solvents were removed under reduced pressure at <40° C. CH$_2$Cl$_2$ and CH$_3$CN were distilled from CaH$_2$ directly prior to application. Pyridine was dried by refluxing with CaH$_2$ and then distilled and stored over molecular sieves (3 Å). Cu(OTf)$_2$ was co-evaporated with toluene (3×10 mL) and dried in vacuo for 2-3 h directly prior to application. N,N'-Diisopropylcarbodiimide, 4-dimethylaminopyridine, piperidine, and anhydrous DMF were used without further conditioning. Optical rotations were measured using a Jasco P-1020 polarimeter. Unless noted otherwise, $^1$H-NMR spectra were recorded in CDCl$_3$ at 300 MHz (Bruker Avance) or at 500 MHz (Bruker ARX-500), $^{13}$C-NMR spectra and two-dimensional experiments were recorded in CDCl$_3$ at 75 MHz (Bruker Avance) or at 125 MHz (Bruker ARX-500). HR FAB-MS determinations were made with the use of JEOL MStation (JMS-700) Mass Spectrometer; matrix m-nitrobenzyl alcohol, with NaI as necessary.

Methyl 2,3-di-O-benzyl-6-O-(3-carboxypropanoyl)-α-D-glycopyranoside (8)

4-Dimethylaminopyridine (DMAP, 32 mg, 0.26 mmol) and succinic anhydride (0.16 g, 1.56 mmol) were added to a stirred solution of methyl 2,3-di-O-benzyl-α-D-glucopyranoside 7 (Bazin et al., *J. Org. Chem.* 1999, 64, 144-152) (0.5 g, 1.3 mmol) in dry pyridine (5 mL) and the resulting mixture was stirred for 16 h at rt (~23° C.) under argon. After that, the reaction mixture was concentrated under the reduced pressure, the residue was dissolved in $CH_2Cl_2$ (30 mL) and washed with water (3×15 mL). The organic phase was separated, dried over $MgSO_4$, filtered and concentrated in vacuo. The residue was purified by column chromatography on silica gel (ethyl acetate-hexane gradient elution) to give the title compound 8 (0.45 g, 0.95 mmol) as a colorless syrup in 71% yield. Analytical data for 8: $R_f$=0.43 (ethyl acetate); $[\alpha]_D^{22}$+7.19° (c=1.0, $CHCl_3$); $^1$H NMR (300 MHz, $CDCl_3$): δ 2.60 (m, 4H, 2×$CH_2$), 3.38 (s, 3H, $OCH_3$), 3.44 (dd, 1H, $J_{2,3}$=9.5 Hz, H-2), 3.51 (dd, 1H, $J_{4,5}$=9.5 Hz, H-4), 3.73 (m, 1H, $J_{5,6b}$=4.8 Hz, H-5), 3.80 (dd, 1H, $J_{2,3}$=9.2 Hz, H-3), 4.26 (dd, 1H, $J_{6a,6b}$=10.0 Hz, H-6a), 4.42 (1H, H-6b), 4.61 (d, 1H, $J_{1,2}$=3.5 Hz, H-1), 4.65 (d, 1H, $J^2$=12.1 Hz, ½$CH_2Ph$), 4.74-4.79 (m, 2H, $CH_2Ph$), 4.99 (d, 1H, J=11.3 Hz, ½$CH_2Ph$), 7.26-7.36 (m, 10H, aromatic) ppm; $^{13}$C NMR (75 MHz, $CDCl_3$): δ, 55.4, 63.7, 69.4, 69.9, 73.3, 75.3, 79.7, 81.0, 98.3, 128.0, 128.1, 128.2, 128.5, 128.6, 128.7, 138.1, 138.6, 172.6, 177.2 ppm; HR FAB MS $[M+Na]^+$ calcd for $C_{25}H_{30}O_9Na$ 497.1788. found 497.1770.

Methyl 2,3-di-O-benzyl-6-O-(4-((S)-2-(9-fluorenyl-methoxyearbonyl)amino-3-(tert-butoxy)-3-oxopropyl)oxy-4-oxobutanoyl)-α-D-glycopyranoside (10)

DMAP (12.7 mg, 0.01 mmol) and N,N'-diisopropylcarbodiimide (DIC, 0.16 mL, 1.04 mmol) were added to a stirred solution of O-tert-butyl N-fluorenylmethoxycarbonyl-L-serine ester 9 (Shiozaki et al., *Tetrahedron*, 2006, 62, 205-225; Peri et al., *Angew. Chem., Int. Ed.* 2007, 46, 3308-3312) (0.19 g, 0.52 mmol) in $CH_2Cl_2$ (4 mL). After 1 h, carboxylic acid derivative 8 (0.29 g, 0.62 mmol) was added and the reaction was stirred for 5-9 h at rt until no further conversion of the starting material could be detected by TLC analysis. The reaction mixture was diluted with $CH_2Cl_2$ (20 mL), washed with water (2×15 mL) and brine (15 mL). The organic phase was separated, dried over $MgSO_4$, filtered and concentrated in vacuo. The residue was purified by column chromatography on silica gel (ethyl acetate-hexane gradient elution) to afford the title compound 10 (0.34 g, 0.41 mmol) as a white powder in 80% yield. Analytical data for 10: $R_f$=0.34 (ethyl acetate/hexane, 1/1, v/v); $[\alpha]_D^{27}$+12.1° (c=1.0, $CHCl_3$); $^1$H NMR (300 MHz, $CDCl_3$): δ, 1.48 (s, 9H, t-Bu), 2.53 (br. s, OH), 2.66 (m, 4H, 2×$CH_2$), 3.37 (s, 3H, $OCH_3$), 3.42 (d, 1H, $J_{2,3}$=9.0, H-2), 3.73 (m, 1H, H-5), 3.78 (dd, 1H, $J_{3,4}$=9.1 Hz, H-3), 4.25 (m, 2H, H-6b, SerC$^\beta$-H), 4.38 (m, 2H, H-6$^a$, SerC$^\beta$-H), 4.44 (m, 2H, $CH_2$Fmoc), 4.52 (m, 1H, SerC$^\alpha$-H), 4.61 (d, 1H, $J_{1,2}$=3.2 Hz, H-1), 4.64 (d, 1H, $J^2$=12.1 Hz, ½$CH_2Ph$), 4.75 (dd, 2H, J=12.0 Hz, $CH_2Ph$), 4.98 (d, 1H, $J^2$=11.3 Hz, ½$CH_2Ph$), 4.75 (d, 1H, $J_{NH,CH}$=8.0 Hz, Ser-NH), 7.27-7.77 (m, 18H, aromatic) ppm; $^{13}$C NMR (125 MHz, $CDCl_3$): δ, 28.1, 29.1, 29.1, 47.3, 54.1, 55.5, 63.9, 64.8, 67.4, 69.4, 70.1, 73.4, 75.7, 79.7, 81.3, 83.3, 98.4, 120.2, 125.4, 125.4, 127.3, 127.9, 128.1, 128.2, 128.3, 128.7, 128.8, 138.2, 138.9, 141.5, 144.0, 144.1, 156.0, 168.5, 171.8, 172.6 ppm; HR FAB MS $[M+Na]^+$ calcd for $C_{47}H_{53}NO_{13}Na$ 862.3415. found 862.3432.

Methyl 2,3-di-O-benzyl-6-O-(4-((S)-2-(9-fluorenyl-methoxyearbonyl)amino-2-carboxyethyl)oxy-4-oxobutanoyl)-α-D-glycopyranoside (11)

Conjugate 10 (0.25 g, 0.29 mmol) was dissolved in TFA/wet $CH_2Cl_2$ (1/5, v/v, 2 mL) and the resulting mixture was stirred for 2 h at rt. After that, the volatiles were evaporated under the reduced pressure, the residue was diluted with $CH_2Cl_2$ (5 mL) and neutralized with triethylamine (until pH ~7). The volatiles were removed under the reduced pressure and the residue was purified by column chromatography on silica gel (ethyl acetate/hexane, 1/1, v/v) to afford the title compound 11 (0.18 g, 0.24 mmol) as a white foam in 81% yield. Analytical data for 11: $R_f$=0.5 (methanol/ethyl acetate, 1/4, v/v); $[\alpha]_D^{26}$+22.5° (c=1.0, $CHCl_3$); $^1$H NMR (500 MHz, $CDCl_3/(CD_3)_2SO$, 2/1, v/v): δ=2.49-2.54 (m, 4H), 3.26 (s, 3H, $OCH_3$), 3.39 (m, 2H), 3.57 (m, 2H), 4.01 (br. s, 1H), 4.12 (m, 2H), 4.22 (m, 2H), 4.32 (dd, 2H, J=6.6 Hz), 4.43 (d, 1H, J=5.1 Hz), 4.60 (s, 2H), 4.76 (m, 2H), 7.24-7.93 (m, 18H, aromatic) ppm; $^{13}$C NMR (75 MHz, $CDCl_3/(CD_3)_2SO$, 2/1, v/v): δ, 28.8, 29.9, 31.1, 47.0, 54.7, 54.8, 63.4, 63.9, 65.3, 65.9, 69.8, 70.2, 71.8, 74.5, 79.4, 81.5, 97.3, 120.5, 125.5, 127.4, 127.5, 127.8, 127.9 (×2), 128.0, 128.3, 128.5, 138.9, 139.6, 141.1, 144.2, 156.0, 172.1, 172.2 ppm; HR FAB MS $[M+Na]^+$ calcd for $C_{43}H_{45}NO_{13}Na$ 806.2789. found 806.2780.

Methyl 2,3-di-O-benzyl-6-O-(4-((S)-2-amino-3-(tert-butoxy)-3-oxopropyl)oxy-4-oxobutanoyl)-α-D-glycopyranoside (12)

Piperidine (0.5 mL) was added dropwise to a solution of monosaccharide 10 (0.1 g, 0.12 mmol) in DMF (2.0 mL) and the resulting mixture was stirred for 20 min at rt. After that, the reaction mixture was concentrated in vacuo and co-evaporated with toluene (×3). The residue was purified by flash column chromatography (ethyl acetate/hexane, 1/1, v/v) to give the title compound 12 (67 mg, 0.1 mmol) as a yellow syrup in 92% yield. Analytical data for 12: $R_f$=0.62 (methanol/ethyl acetate, 1/9, v/v); $[\alpha]_D^{26}$+17.3° (c=1.0, $CHCl_3$); $^1$H NMR (500 MHz, $CDCl_3$): δ=1.49 (s, 9H, t-Bu), 2.52-2.66 (m, 3H), 2.73-2.78 (m, 1H), 3.02 (broad s, 1H, OH), 3.38 (s, 3H, $OCH_3$), 3.46 (d, 1H, $J_{2,3}$=9.4 Hz, H-2), 3.50 (ddd, 1H, $J_{4,5}$=9.5 Hz, H-4), 3.75 (m, 2H, H-5, Ser-C$^\beta$H), 3.80 (m, 2H, H-3, Ser-C$^\beta$H), 4.18 (dd, 1H, $J_{6a,6b}$=10.19 Hz, H-6a), 4.46 (m, 1H, Ser-C$^\alpha$H), 4.52 (dd, 1H, $J_{5,6b}$=4.19 Hz, H-6b), 4.61 (d, 1H, $J_{1,2}$=3.53 Hz, H-1), 4.65 (d, 1H, $J^2$=12.5 Hz, ½$CH_2Ph$), 4.77 (dd, 2H, J=11.5 Hz, $CH_2Ph$), 4.99 (d, 1H, $J^2$=9.0 Hz, ½$CH_2Ph$), 6.49 (d, 1H, $J_{NH,CH}$=6.95 Hz, Ser-NH), 7.27-7.31 (m, 10H, aromatic) ppm; $^{13}$C NMR (125 MHz, $CDCl_3$): δ, 28.2, 29.8, 31.0, 31.1, 55.5, 55.7, 63.3, 63.6, 69.5, 69.8, 73.5, 75.9, 79.8, 81.5, 83.0, 98.5, 128.1, 128.2, 128.3, 128.4, 128.7 (×2), 138.2, 138.7, 169.6, 172.0, 173.1 ppm; HR FAB MS $[M+Na]^+$ calcd for $C_{32}H_{43}NO_{11}Na$ 640.2734. found 640.2741.

Methyl 2,3-di-O-benzyl-6-O-(4-((S)-2-amino-2-carboxyethyl)oxy-4-oxobutanoyl)-α-D-glycopyranoside (13)

Conjugate 12 (0.1 g, 0.12 mmol) was dissolved in TFA/wet $CH_2Cl_2$ (1/5, v/v, 2 mL) and stirred for 2 h. Upon completion as assessed by TLC analysis, solvents were evaporated in vacuo. The residue was dissolved in $CH_2Cl_2$ (5 mL) and neutralized with triethylamine (until pH≈7). Solvents were removed under the reduced the pressure. The residue was subjected to column chromatography on silica gel (methanol-ethyl acetate gradient elution) to obtain product 13 (50 mg, 0.09 mmol) as white foam in 75% yield. Analytical data for 13: $R_f$=0.5 (methanol/ethyl acetate, 1/4, v/v); $^1$H NMR (500 MHz, $D_2O$): δ, 1.68 (m, 2H), 1.82 (m, 3H), 2.73 (m, 4H), 3.19 (dd, 3H, J=5.7 Hz), 3.4 (s, 3H, $OCH_3$), 3.58 (ddd, 2H, J=9.5, 10.0 Hz), 3.80 (dd, 1H, J=9.2 Hz), 3.87 (d, 3H, J=4.7 Hz), 4.33-4.37 (m, 2H, J=4.7 Hz), 4.54 (d, 1H, J=10.9 Hz), 7.44 (s, 10H, aromatic) ppm; $^{13}$C NMR (125 MHz, $D_2O$): δ, 21.9, 22.6, 29.5, 30.5, 44.9, 55.4, 62.4, 69.8, 73.4, 75.5, 79.1, 81.1, 97.8, 128.7, 128.8, 129.0, 129.1, 137.7, 137.9, 174.5, 175.1, 176.2 ppm; HR FAB MS [M+Na]$^+$ calcd for $C_{28}H_{35}NO_{11}Na$ 584.2108. found 584.2104.

Methyl 4,6-O-(p-methoxybenzylidene)-2,3-di-O-tetradecanoyl-α-D-glucopyranoside (15)

Myristoyl chloride (2.34 mL, 8.67 mmol) and DMAP (70 mg, 0.57 mmol) were added to a stirred solution of methyl 4,6-O-(p-methoxybenzylidene)-α-D-glucopyranoside 14 (Christ et al., *Science*, 1995, 268, 80-83) (1.0 g, 2.89 mmol) in pyridine (15 mL) at 0° C. The mixture was stirred under an atmosphere of argon for 16 h. Upon completion, the reaction mixture was concentrated in vacuo. The residue was dissolved in $CH_2Cl_2$ (30 mL), and washed with 1N HCl (2×15 mL), water (2×15 mL) and brine (15 mL). The organic phase was separated, dried over $MgSO_4$, filtered and concentrated in vacuo. The residue was purified by column chromatography on silica gel (ethyl acetate-hexane gradient elution) to afford derivative 15 (1.81 g, 2.48 mmol) as a white foam in 86% yield. Analytical data for 15: $R_f$=0.47 (ethyl acetate/hexane, 3/7, v/v); $[α]_D^{23}$+23.6° (c=1.0, $CHCl_3$); $^1$H NMR (300 MHz, $CDCl_3$): δ, 0.88 (t, 6H, 2×$CH_3$), 1.26 (br. s, 40H, 20×$CH_2$), 1.59 (m, 4H, 2×$CH_2$), 2.29 (m, 4H, 2×$CH_2$), 3.40 (s, 3H, $OCH_3$), 3.62 (dd, 1H, $J_{4,5}$=9.7 Hz, H-4), 3.75 (dd, 1H, $J_{6a,6b}$=10.2 Hz, H-6a), 3.78 (s, 3H, $OCH_3$), 3.92 (m, 1H, H-5), 4.28 (dd, 1H, $J_{5,6b}$=4.7 Hz, H-6b), 4.82-2.94 (m, 2H, H-1, 2), 5.46 (s, 1H, >CHPh), 5.60 (dd, 1H, $J_{3,4}$=9.7 Hz, H-3), 6.86 (d, 2H, J=8.8 Hz, aromatic), 7.25 (d, 2H, J=8.7 Hz, aromatic) ppm; $^{13}$C NMR (75 MHz, $CDCl_3$): δ, 14.3, 22.9, 25.1, 25.3, 29.2 (×2), 29.4, 29.5 (×2), 29.6, 29.7, 29.8, 29.9, 32.1, 34.3, 34.5, 55.4, 55.5, 62.5, 68.8, 68.9, 71.6, 76.8, 77.2, 77.6, 79.5, 97.8, 101.6, 113.7, 127.6, 129.6, 160.2, 172.6, 173.4 ppm; HR FAB MS [M+Na]$^+$ calcd for $C_{43}H_{72}O_9Na$ 755.5074. found 755.5090.

Methyl 4-O-p-methoxybenzyl-3-O-tetradecanoyl-α-D-glucopyranoside (16)

A 1 M solution of $BH_3$-THF in tetrahydrofuran (5 mL, 5 mmol) was mixed with compound 15 (0.75 g, 1.02 mmol) and the resulting mixture was stirred for 10 min at rt under argon. Freshly conditioned copper(II) trifluoromethanesulfonate (18 mg, 0.05 mmol) was added, and the reaction mixture was stirred for 2 h at rt. After that, the reaction mixture was cooled to 0° C. and then quenched by sequential addition of triethylamine (0.14 mL, 1 mmol) and methanol (1.8 mL). The resulting mixture was concentrated under the reduced pressure followed by co-evaporation with methanol. The residue was purified by flash column chromatography on silica gel (ethyl acetate-hexane gradient elution) to give the title compound 16 (0.35 g, 0.67 mmol) as white solid in 67% yield. Analytical data for 16: $R_f$=0.40 (ethyl acetate/hexane, 7/3, v/v); $[α]_D^{22}$+ 78.5° (c=1.0, $CHCl_3$); $^1$H NMR (300 MHz, $CDCl_3$): δ=0.88 (t, 3H, J=7.02 Hz, $CH_3$), 1.24 (br. s, 20H, 10×$CH_2$), 1.63 (m, 2H, $CH_2$), 1.97 (br. s, 1H, OH), 2.23-3.82 (m, 3H, $CH_2$, OH), 3.41 (s, 3H, $OCH_3$), 3.52-3.82 (m, 5H, H-2, 4, 5, 6a, 6b), 3.79 (s, 3H, $OCH_3$), 4.57 (dd, 2H, J=12.4 Hz, $CH_2$Ph), 4.75 (d, 1H, $J_{1,2}$=3.7 Hz, H-1), 5.30 (dd, 1H, J=9.1 Hz, H-3), 6.85 (d, 2H, J=8.6 Hz, aromatic), 7.20 (d, 2H, J=8.6 Hz, aromatic) ppm; $^{13}$C NMR (75 MHz, $CDCl_3$): δ=14.3, 22.9, 25.1, 29.3, 29.5 (×2), 29.6, 29.7, 29.8, 29.9, 32.1, 34.7, 55.4, 55.5, 61.7, 71.0, 71.9, 74.3, 74.9, 99.6, 114.0, 129.6, 130.1, 159.5, 174.3 ppm; HR FAB MS [M+Na]$^+$ calcd for $C_{29}H_{48}O_8Na$ 547.3247. found 547.3254.

Methyl 6-O-(3-carboxypropanoyl)-4-O-p-methoxybenzyl-2,3-di-O-tetradecanoyl-α-D-glucopyranoside (17)

DMAP (8.1 mg, 0.06 mmol) and succinic anhydride (67 mg, 0.67 mmol) were added to a stirred solution of derivative 16 (0.35 g, 0.67 mmol) in dry pyridine (5 mL) and the resulting mixture was stirred for 16 h at rt under argon. After that, myristoyl chloride (0.21 ml, 0.80 mmol) was added dropwise, and the reaction mixture was stirred for 2 h at rt. After that, the resulting mixture was concentrated under the reduced pressure. The residue was dissolved in $CH_2Cl_2$ (30 mL) and washed successively with 1N HCl (2×15 mL), water (2×15 mL) and brine (15 mL). The organic phase was separated, dried over $MgSO_4$, filtered and concentrated in vacuo. The residue was purified by column chromatography on silica gel (ethyl acetate-hexane gradient elution) to give compound 17 (0.43 g, 0.52 mmol) as white syrup in 79% yield. Analytical data for 17: $R_f$=0.55 (ethyl acetate-hexane 1/1, v/v); $[α]_D^{24}$+ 42.4° (c=1.0, $CHCl_3$); $^1$H NMR (300 MHz, $CDCl_3$): δ, 0.87 (t, 6H, 2×$CH_3$), 1.25 (br. s, 40H, 20×$CH_2$), 1.59 (m, 4H, 2×$CH_2$), 2.26 (m, 2H, $CH_2$), 2.33 (m, 2H, $CH_2$), 2.61 (m, 4H, 2×$CH_2$), 3.36 (s, 3H, $OCH_3$), 3.59 (dd, 1H, $J_{4,5}$=9.5 Hz, H-4), 3.90 (m, 1H, H-5), 4.28 (dd, 2H, $J_{5,6b}$=4.4 Hz, $J_{6a,6b}$=11.5 Hz, H-6a, 6b), 4.44 (d, 1H, $J^2$=10.7 Hz, ½$CH_2$Ph), 4.54 (d, 1H, $J^2$=10.7, ½$CH_2$Ph), 4.87 (m, 2H, H-1, 2), 5.55 (dd, 1H, $J_{3,4}$=9.5 Hz, H-3), 6.84 (d, 2H, J=8.7 Hz, aromatic), 7.16 (d, 2H, J=8.6 Hz, aromatic) ppm; $^{13}$C NMR (75 MHz, $CDCl_3$): δ, 14.3, 22.8, 25.1, 28.8, 29.2, 29.3, 29.4 (×2), 29.5, 29.6, 29.7, 29.8, 32.1, 34.2, 34.5 (×3), 55.4, 62.7, 68.6, 71.8, 71.9, 74.3, 75.7, 96.9, 114.0, 129.5, 129.8, 159.6, 171.7, 172.8, 173.7 ppm; HR FAB MS [M+Na]$^+$ calcd for $C_{47}H_{78}O_{12}Na$ 857.5391. found 857.5410.

Methyl 6-O-(4-((S)-2-(9-fluorenylmethoxycarbonyl) amino-3-(tert-butoxy)-3-oxopropyl)oxy-4-oxobutanoyl)-2,3-di-O-tetradecanoyl-α-D-glucopyranoside (18)

DMAP (9.5 mg, 0.07 mmol) and DIC (0.12 mL, 0.78 mmol) were added to a stirred solution of O-tert-butyl-N-fluorenylmethoxycarbonyl-L-serine 9 (Shiozaki et al., *Tetrahedron*, 2006, 62, 205-225; Pen et al., *Angew. Chem., Int. Ed.*, 2007, 46, 3308-3312) (0.15 g, 0.39 mmol) in $CH_2Cl_2$ (3 mL). After 1 h, the carboxylic acid derivative 17 (0.39 g, 0.46 mmol) was added and the reaction was stirred for 5-9 h at rt no further conversion of the starting material could be detected by TLC analysis. The reaction mixture was diluted with $CH_2Cl_2$ (20 mL), washed with water (2×10 mL) and brine (10 mL). The organic phase was separated, dried over $MgSO_4$, filtered and concentrated in vacuo. The residue was purified by column chromatography on silica gel (ethyl acetate-hexane gradient elution) to afford the title compound 18 (0.38 g, 0.32 mmol) as a white solid in 83% yield. Analytical data for 18: $R_f$=0.5 (ethyl acetate/hexane, 3/7, v/v); $[\alpha]_D^{24}$+25.7° (c=1.0, $CHCl_3$); $^1$H NMR (300 MHz, $CDCl_3$): δ, 0.88 (t, 6H, 2×$CH_3$), 1.25 (br. s, 40H, 20×$CH_2$), 1.49 (s, 9H, t-Bu), 1.59 (m, 4H, 2×$CH_2$), 1.59 (m, 4H, 2×$CH_2$), 2.30 (m, 4H, 2×$CH_2$), 3.37 (s, 3H, $OCH_3$), 3.48 (dd, 1H, $J_{4,5}$=9.5 Hz, H-4), 3.76 (s, 3H, $OCH_3$), 3.90 (m, 1H, H-5), 4.16-4.26 (m, 3H, H-6a, 6b, Ser-$C^\beta$H), 4.35-4.55 (m, 6H, $CH_2$Ph, Ser-$C^\alpha$H, Ser-$C^\beta$H, $CH_2$Fmoc), 4.90 (m, 2H, H-1, 2), 5.58 (dd, 1H, $J_{3,4}$=9.7 Hz, H-3), 5.82 (d, 1H, $J_{NH,CH}$=8.3 Hz, Ser-NH), 6.18-7.77 (m, 12H, aromatic) ppm; $^{13}$C NMR (75 MHz, $CDCl_3$): δ, 14.3, 22.8, 25.0, 28.0, 28.8, 29.0, 29.3 (×2), 29.4, 29.5, 29.6, 29.8, 32.0, 34.2, 34.4, 47.2, 54.0, 55.3, 62.6, 67.4, 68.5, 71.7, 71.8, 74.3, 83.0, 96.8, 113.9, 120.1, 125.4, 127.2, 127.8, 129.3, 129.6, 141.4, 144.0, 155.9, 159.5, 168.4, 171.5, 172.7, 173.5 ppm; HR FAB MS $[M+Na]^+$ calcd for $C_{69}H_{101}NO_{16}Na$ 1222.7018. found 1222.7023.

Methyl 6-O-(4-((S)-2-(9-fluorenylmethoxyearbonyl) amino-2-carboxyethyl)oxy-4-oxobutanoyl)-2,3-di-O-tetradecanoyl-α-D-glucopyranoside (19)

Compound 18 (0.2 g, 0.16 mmol) was dissolved in TFA/wet $CH_2Cl_2$ (1/5, v/v, 4 mL) and stirred for 2 h at rt. After that, the volatiles were evaporated in vacuo, the residue was diluted with $CH_2Cl_2$ (5 mL) and neutralized with triethylamine (until pH ~7). The volatiles were removed under the reduced the pressure and the residue was purified by column chromatography on silica gel (ethyl acetate/hexane, 1/1, v/v) to afford the title compound 19 (0.13 g, 0.12 mmol) as a white foam in 75% yield. Analytical data for 19: $R_f$=0.5 (methanol-ethyl acetate 1/9, v/v); $^1$H NMR (300 Hz, $CDCl_3$): δ, 0.88 (t, 6H, 2×$CH_3$), 1.25 (br. s, 40H, 20×$CH_2$), 1.58 (m, 4H, 2×$CH_2$), 2.33 (m, 4H, 2×$CH_2$), 3.27 (br. s, 4H, 2×$CH_2$), 3.27 (br. s, 1H, OH), 3.38 (s, 3H, $OCH_3$), 3.47 (dd, 1H, $J_{45}$=9.4 Hz, H-4), 3.83 (m, 1H, H-5), 4.21-4.51 (m, 7H, H-6a, 6b, Ser-$C^\beta H_2$, Ser-$C^\alpha$H, $CH_2$Fmoc), 4.86 (m, 1H, H-2), 4.90 (br. s, 1H, H-1), 5.31 (dd, 1H, $J_{3,4}$=9.1 Hz, H-3), 5.96 (br. s, 1H, Ser-NH), 7.27-7.76 (m, 8H, aromatic) ppm; $^{13}$C NMR (75 MHz, $CDCl_3$): δ, 25.0, 25.1, 28.9, 29.3 (×2), 29.4, 29.5, 29.6, 29.8, 29.9, 32.1, 34.2, 34.5, 47.2, 55.5, 62.9, 64.3, 67.6, 69.4, 69.6, 69.9, 71.2, 72.7, 77.4, 96.8, 114.1, 120.2, 124.9, 125.3, 127.3, 127.9, 141.4, 143.8, 143.9, 171.7, 171.8, 174.3, 174.6, 175.1 ppm; HR FAB MS $[M+Na]^+$ calcd for $C_{57}H_{85}NO_{15}Na$ 1046.5817. found 1045.5822.

Methyl 6-O-(3-carboxypropanoyl)-4-O-p-methoxybenzyl-2,3-di-O-tetradecanyl-α-D-glucopyranoside (22)

DMAP (7.0 mg, 0.05 mmol) and succinic anhydride (71 mg, 0.70 mmol) were added to a stirred solution of methyl 4-O-p-methoxybenzyl-2,3-di-O-tetradecanyl-α-D-glucopyranoside 21 (Price et al., *Proc. Natl. Acad. Sci., USA*, 1995, 92, 7352-7356) (0.40 g, 0.56 mmol) in dry pyridine (5 mL) and the resulting reaction mixture was stirred for 16 h at rt under argon. After that, the reaction mixture was concentrated under the reduced pressure. The residue was dissolved in $CH_2Cl_2$ (30 mL) and washed successively with 1N HCl (2×15 mL), water (2×15 mL) and brine (15 mL). The organic phase was separated, dried over $MgSO_4$, filtered and concentrated in vacuo. The residue was purified by column chromatography on silica gel (ethyl acetate-hexane gradient elution) to give the title compound 22 (0.41 g, 0.50 mmol) as a colorless syrup in 89% yield. Analytical data for 22: $R_f$=0.55 (ethyl acetate/hexane, 7/3, v/v); $[\alpha]_D^{24}$+42.9° (c=1.0, $CHCl_3$); $^1$H NMR (300 MHz, $CDCl_3$): δ, 0.88 (t, 6H, 2×$CH_3$), 1.26 (br. s, 40H, 22×$CH_2$), 1.63 (m, 4H, 2×$CH_2$), 2.64 (m, 2H, 2×$CH_2$), 3.30 (dd, 1H, $J_{2,3}$=9.7 Hz, H-2), 3.38 (s, 3H, $OCH_3$), 3.39 (m, H-4), 3.59-3.76 (m, 5H, H-3, 5, $OCH_2$, $OCH_2^a$), 3.80 (s, 3H, $OCH_3$), 3.86 (m, 1H, $OCH_2^b$), 4.28 (m, 2H, $J_{5,6b}$=4.7 Hz, $J_{5,6a}$=2.3 Hz, $J_{6a,6b}$=12.0 Hz, H-6a, 6b), 4.49 (d, 1H, $J^2$=10.5 Hz, ½$CH_2$Ph), 4.76 (d, 1H, $J_{1,2}$=3.5 Hz, H-1), 4.81 (d, 1H, $J^2$=10.5 Hz, ½$CH_2$Ph), 6.89 (d, 2H, J=8.9 Hz, aromatic), 7.22 (d, 2H, J=9.7 Hz, aromatic) ppm; $^{13}$C NMR (125 MHz, $CDCl_3$): δ=14.3, 22.9, 26.2, 26.5, 28.8, 28.9, 29.5, 29.7, 29.8, 29.9 (×2), 30.3, 30.8, 32.1, 55.3, 55.5, 63.6, 68.8, 72.0, 74.1, 74.8, 80.9, 81.9, 98.1, 114.1, 130.1, 130.4, 159.6, 172.0, 176.5 ppm; HR FAB MS $[M+Na]^+$ calcd for $C_{47}H_{82}O_{10}Na$ 829.5805. found 829.5806.

Methyl 6-O-(4-((S)-2-(9-fluorenylmethoxycarbonyl) amino-3-(tert-butoxy)-3-oxopropyl)oxy-4-oxobutanoyl)-2,3-di-O-tetradecanyl-α-D-glucopyranoside (23)

DMAP (6.2 mg, 0.05 mmol) and DIC (0.16 mL, 1.01 mmol) were added to a stirred solution of O-tert-butyl-N-fluorenylmethoxycarbonyl-L-serine 9 (0.39 g, 0.60 mmol) in $CH_2Cl_2$ (3 ml). After 1 h, the carboxylic acid derivative 22 (0.41 g, 0.50 mmol) was added and the reaction was stirred for 5-9 h until no further conversion of the starting material could be detected by TLC analysis. The reaction mixture was diluted with $CH_2Cl_2$ (20 mL), washed with water (2×10 mL) and brine (10 mL). The organic phase was separated, dried over $MgSO_4$, filtered and concentrated in vacuo. The residue was purified by column chromatography on silica gel (ethyl acetate-hexane gradient elution) to afford the title compound 23 (0.47 g, 0.40 mmol) as a colorless amorphous solid in 79% yield. Analytical data for 23: $R_f$=0.43 (ethyl acetate/hexane, 3/7, v/v); $[\alpha]_D^{24}$+36.1° (c=1.0, $CHCl_3$); $^1$H NMR (300 MHz, $CDCl_3$): δ, 0.88 (t, 6H, 2×$CH_3$), 1.17 (m, 40H, 20×$CH_2$), 1.38 (s, 9H, t-Bu), 1.54 (m, 4H, 2×$CH_2$), 2.53 (m, 4H, 2×$CH_2$), 3.18 (dd, 1H, $J_{2,3}$=9.7 Hz, H-2), 3.26 (s, 3H, $OCH_3$), 3.28 (m, 1H, H-4), 3.42-3.66 (m, 5H, H-3, 5, $OCH_2$, $OCH_2^a$), 3.67 (s, 3H, $OCH_3$), 3.79 (m, 1H, $OCH_2^b$), 4.11-4.46 (m, 8H, H-6a, 6b, ½$CH_2$Ph, Ser-$C^\alpha$H, Ser-$C^\beta H_2$, $CH_2$Fmoc), 4.66 (d, 1H, $J_{1,2}$=3.3 Hz, H-1), 4.71 (d, 1H, $J^2$=10.5 Hz, ½$CH_2$Ph), 5.71 (d, 1H, $J_{NH,CH}$=8.1 Hz, Ser-NH), 6.75-7.64 (m, 12H, aromatic) ppm; $^{13}$C NMR (75 MHz, $CDCl_3$): δ, 14.2, 22.8, 26.1, 26.4, 28.0, 28.9, 29.5, 29.6, 29.7, 29.8, 30.2, 30.7, 32.0, 47.0, 54.0, 55.2, 55.3, 64.7, 67.3, 68.6, 71.8, 73.8, 74.6, 80.8, 81.8, 83.0, 97.9, 99.7, 113.9, 120.1, 125.2, 125.3, 127.2, 127.8, 129.9, 130.3, 141.4, 142.5, 143.9, 155.9, 159.4, 168.4, 171.7, 172.0, 181.3 ppm; HR FAB MS $[M+Na]^+$ calcd for $C_{69}H_{105}NO_{14}Na$ 1194.7433. found 1194.7433.

Methyl 6-O-(4-((S)-2-(9-fluorenylmethoxycarbonyl) amino-2-carboxyethyl)oxy-4-oxobutanoyl)-2,3-di-O-tetradecanyl-α-D-glucopyranoside (24)

Conjugate 23 (0.2 g, 0.17 mmol) was dissolved in TFA/wet $CH_2Cl_2$ (1/5, v/v, 4 mL) and the resulting mixture was stirred for 2 h at rt. After that, the volatiles were evaporated under the reduced pressure, the residue was diluted with $CH_2Cl_2$ (5 mL) and neutralized with triethylamine (until pH ~7). The volatiles were removed under the reduced pressure and the residue was purified by column chromatography on silica gel (ethyl acetate/hexane 1/1, v/v) to obtain the title compound 24 (0.13 g, 0.14 mmol) as a white amorphous solid in 81% yield. Analytical data for 24: $R_f$=0.58 (methanol/ethyl acetate, 1.5/8.5, v/v); $[\alpha]_D^{26}$+34.9° (c=1.0, $CHCl_3$); $^1$H NMR (500 MHz, $CDCl_3$/$(CD_3)_2$SO, 2/1, v/v): δ, 0.78 (t, 6H, 2×$CH_3$), 1.45 (br. s, 40H, 20×$CH_2$), 1.47 (m, 4H, 2×$CH_2$), 2.5 (m, 4H, 2×$CH_2$), 3.10 (dd, 1H, $J_{2,3}$=9.4 Hz, H-2), 3.22-3.33 (m, 7H), 3.41-3.51

(m, 3H), 3.55 (m, 1H, H-5), 3.64 (t, 2H, J=6.7 Hz), 4.14-4.32 (m, 7H), 4.42 (d, 1H, J=9.5 Hz), 4.63 (d, 1H, $J_{1,2}$=3.2 Hz, H-1), 6.52 (br. s, 1H, Ser-NH), 7.22-7.82 (m, 8H, aromatic) ppm; $^{13}$C NMR (125 MHz, CDCl$_3$/(CD$_3$)$_2$SO, 2/1, v/v): δ, 13.6, 21.9, 25.4, 25.5, 28.6, 28.8, 28.9, 29.0, 29.5 (×2), 31.2, 39.0, 39.2, 39.3, 39.5, 39.7, 39.8 (×2), 39.9, 40.0, 40.1, 46.6, 54.3, 63.4, 65.6, 69.2, 69.4, 70.6, 72.7, 79.6, 80.7, 97.3, 119.4, 124.6, 124.8, 126.6, 127.1, 140.1, 143.4, 155.4, 171.3, 171.6, 178.3, 178.7 ppm; HR FAB MS [M+Na]$^+$ calcd for $C_{57}H_{89}NO_{13}Na$ 1018.6232. found 1018.6182.

Example 2

Compound Analysis

Preparation of Compounds for Cellular Treatment.

Synthetic compounds in solid form were dissolved in tetrahydrofuran (THF), aliquotted in small volumes, vacuum-centrifuged for 1 h and stored at −80° C. as dry compounds. For cellular treatment, an aliquot was dissolved in an appropriate volume of dimethylsulfoxide (DMSO) to give a concentrated working stock solution. This stock solution was further diluted in DMSO to give the desired concentration range. The final concentration of DMSO in the cell treatments was always maintained at 0.6%. Concentrations of Fmoc-containing compounds were verified by absorbance using an extinction coefficient of 7800 M$^{-1}$ cm$^{-1}$ at 301 nm.

Cell Culture and LPS Antagonism Assays.

THP-1 cells were obtained from ATCC (Manassas, Va.) and maintained in RPMI-1640 culture medium (HyClone, Logan, Utah) containing 2 mM L-glutamine, 25 mM HEPES, 1.5 g/L sodium bicarbonate, 10% fetal bovine serum (FBS) (HyClone), 50 units/mL penicillin, 50 µg/mL streptomycin (HyClone), and 50 µM β-mercaptoethanol at 37° C. in 5% CO$_2$. For cellular assay, THP-1 monocytes were centrifuged and resuspended in a fresh growth medium to a cell density of 5×10$^5$ cells/mL Cells were then seeded in a 48-well plate and differentiated into adherent macrophages by treatment with 10 ng/mL phorbol 12-myristate 13-acetate (PMA) (Sigma) for 24 h at 37° C. in 5% CO$_2$. The non-adherent cells were removed and the adherent cells were washed and replenished with reduced FBS growth medium. For the two wells set aside for calculating percent differentiation, the cells were washed with PBS (Hyclone) prior to removal by 0.25% trypsin-EDTA. Cells in a separate well were removed with 0.25% trypsin and counted under the microscope using a hemocytometer to determine the number of adherent macrophages. For the remaining wells, the cells were pre-incubated with LPS antagonist compounds at different concentrations for 30 min followed by addition of 10 ng/mL ultrapure LPS from *E. coli* K12 (InvivoGen, San Diego, Calif.) for 6 h at 37° C. in 5% CO$_2$. 0.6% DMSO was used as a control. The cell medium was collected and stored at −20° C. until analyzed by ELISA for secreted TNFα production.

Cell Viability Measurements.

Cell viability was monitored using an XTT [2,3-bis(2-methoxy-4-nitro-5-sulfophenyl)-2H-tetrazolium-5-carboxanilide] assay. Macrophage metabolic activity was assessed by probing mitochondrial reduction of XTT (Sigma) which is a measure of viability (or toxicity) in response to the synthetic antagonists. Following 6 h treatment with antagonist compounds and LPS, the macrophages were washed with PBS (Hyclone) and incubated with XTT (0.33 mg/mL) and phenazine methosulfate (PMS) (8.3 µM) (Acros, Morris Plains, N.J.) to a final concentration of 0.33 mg/mL and 8.3 µM respectively for 2 h at 37° C. in 5% CO$_2$. The cellular toxicity was then assessed in a platereader using absorbance of reduced XTT at 467 nm.

Compound Evaluation.

Figure 2:
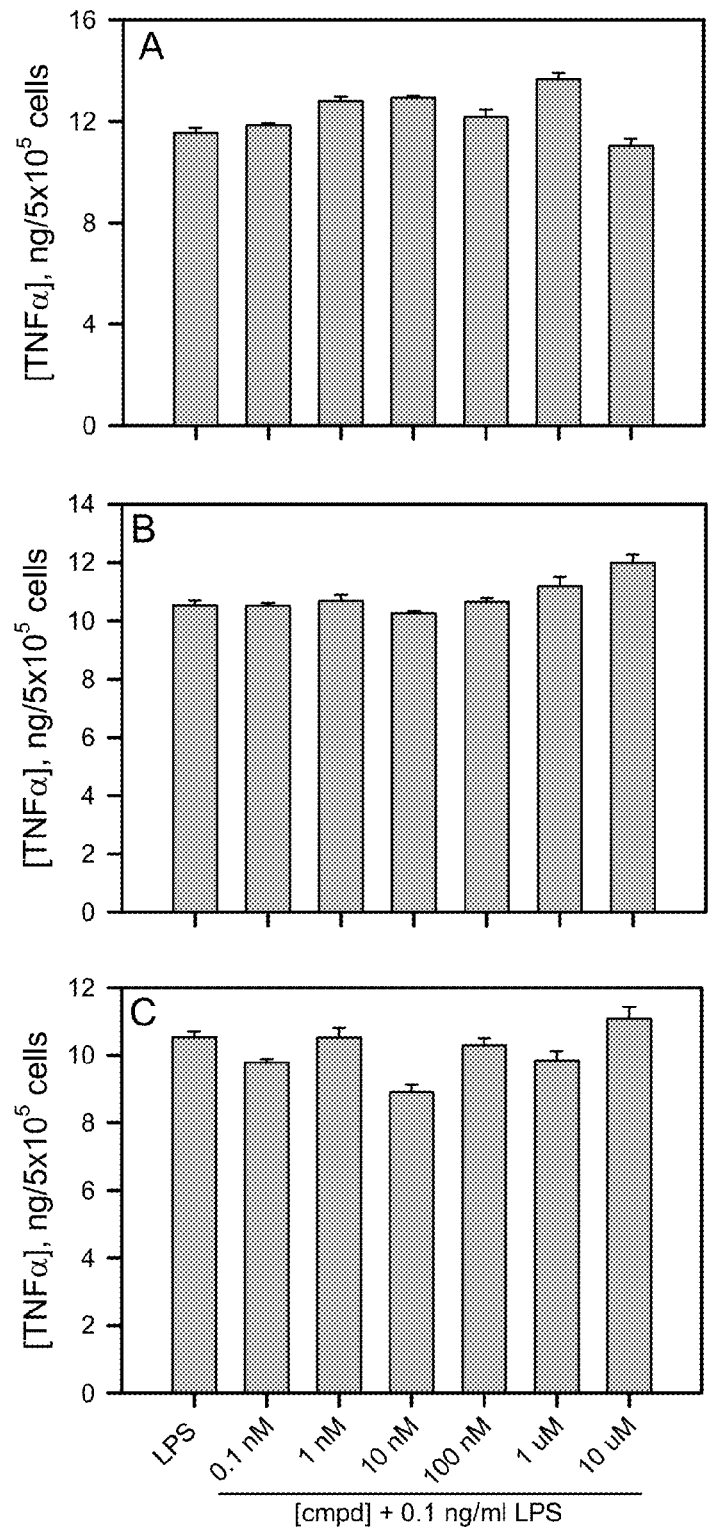
FIG. 2. Compounds 10, 12, and 13 do not display LPS antagonistic activity. THP-1 human monocytes were treated as described in Example 2 with 10 ng/mL PMA for 24 h at 37° C. and 5% $CO_2$. The medium was then removed and adherent macrophages were further treated as described with increasing concentrations of compounds 10 (panel A), 12 (panel B) and 13 (panel C) for 30 min followed incubation with 10 ng/mL LPS for 6 h. Secreted TNFα was measured by ELISA and the levels (ng/mL) were reported on the y-axis after normalization by the number of counted macrophages (cells/mL). Error bars represent the standard error (std. err.) for 3 different TNFα measurements from each cell treatment.
Figure 3:
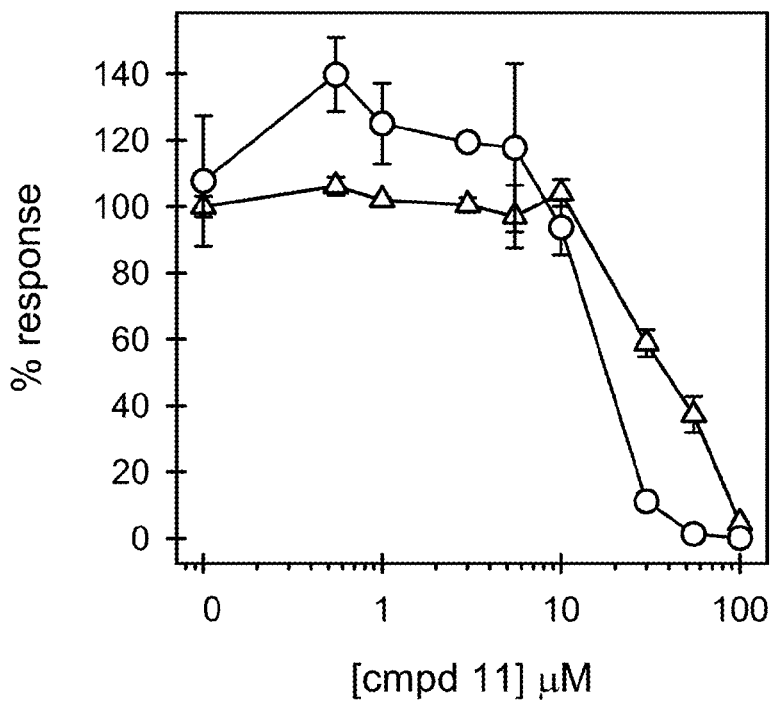
FIG. 3. Compound 11 displays LPS antagonistic activity and cell toxicity. THP-1 macrophages were treated as described in the FIG. 2 legend with increasing concentrations of compound 11. Secreted TNFα levels (circles) are the average +/−std. err. for n=2 trials and are reported as the % response of LPS in the absence of antagonist compound Immediately following the cell treatment described above and in FIG. 2 legend, macrophage viability (triangles) (n=2 trials) was determined by XTT reduction as described in Example 2. Cell viability is presented as a percentage of the cell viability measured in the absence of antagonists.

The inhibitory activity of compounds 10-13 on LPS-induced TNFα production was investigated in vitro using THP-1 macrophages prepared as described above. THP-1 cells are an excellent system for studying inflammatory processes and serve as a model for peripheral monocytes/macrophages and their responses to bacterial infection. Compounds 10, 12, and 13 exhibited no inhibitory activity against LPS-induced TNFα production in the concentration range of 0.1 nM to 10 µM (FIG. 2A-C). These compounds were also tested in the absence of LPS and demonstrated no agonist activity. Compound 11, which has a free carboxylic group, was able to significantly inhibit LPS-induced TNFα production at concentrations greater than 10 µM (FIG. 3). Unfortunately, cell viability measurements using an XTT reduction assay indicated that compound 11 was toxic to the cells in the 30-100 µM range. Although there was a notable gap between inhibition and toxicity at 30 and 50 µM, the similarities between the inhibition and toxicity curves suggested that much of the antagonistic activity by 11 was related to toxicity.

Figure 4:
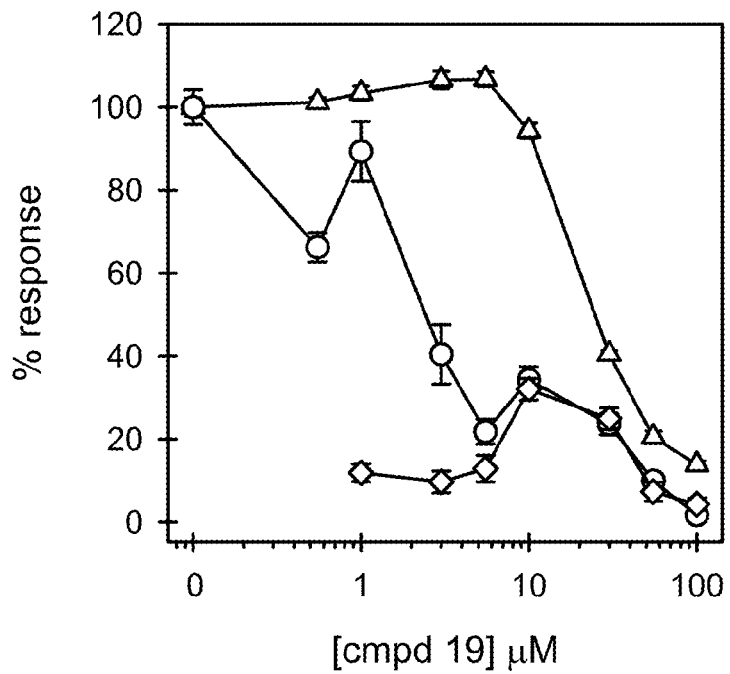
FIG. 4. Compound 19 displays highly potent LPS antagonistic activity. THP-1 macrophages were treated in 3 separate experiments as described in the FIG. 2 legend with increasing concentrations of compound 19. Secreted TNFα levels were determined in the presence (circles) (n=9 trials) and absence (diamonds) (n=6 trials) of LPS. Cell viability (triangles) (n=9 trials) was also assessed and presented as described in the FIG. 3 legend.

Comparative studies were then performed using compounds 19 and 24, lipidated and alkylated analogs of compound 11, respectively. In addition, as a comparison point, the standard positive control compound 4 (Peri et al.) was obtained. Lipidated compound 19 displayed a marked improvement in LPS-antagonistic ability Inhibition of LPS-induced TNFα was found beginning at 550 nM 19 (FIG. 4). A reproducible biphasic response was consistently seen in the activity of 19. This may indicate multiple binding sites on the macrophages, both higher and lower affinity for the antagonist compound. 80% of the LPS response was blocked at 5 µM compound 19 with no observable toxicity. Cell viability began to be compromised at 10 µM and some agonist activity was found in the 10-30 µM range (FIG. 4).

Figure 5:
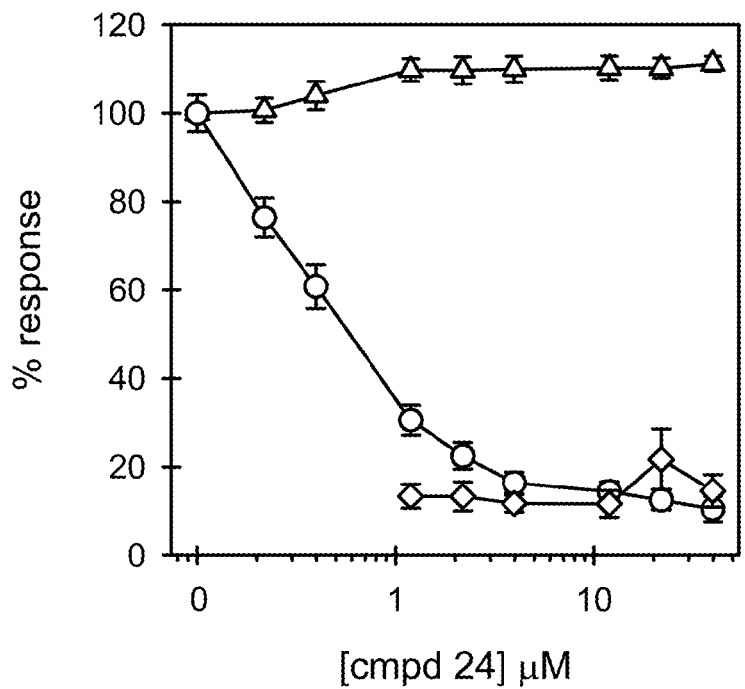
FIG. 5. Compound 24 displays significant LPS antagonistic activity without toxicity. THP-1 macrophages were treated in 4 separate experiments as described in the FIG. 2 legend with increasing concentrations of compound 24. Secreted TNFα levels were determined in the presence (circles) (n=12 trials) and absence (diamonds) (n=8 trials) of LPS. Cell viability (triangles) (n=12 trials) was also assessed and presented as described in the FIG. 3 legend.
Figure 6:
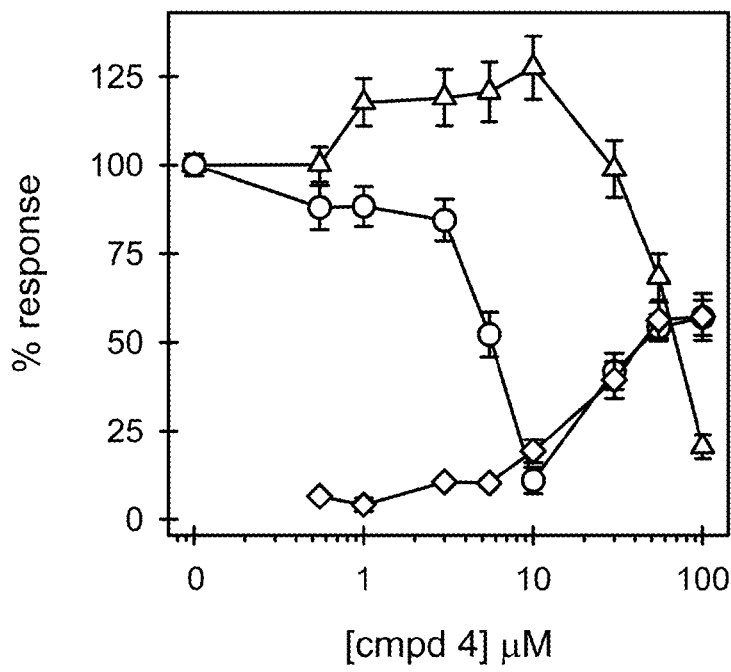
FIG. 6. LPS antagonistic activity displayed by compound 4. THP-1 macrophages were treated in 3 separate experiments as described in the FIG. 2 legend with increasing concentrations of compound 4. Secreted TNFα levels were determined in the presence (circles) (n=8 trials) and absence (diamonds) (n=5 trials) of LPS. Cell viability (triangles) (n=11 trials) was also assessed and presented as described in the FIG. 3 legend.

The alkylated compound 24 was found to be a very effective inhibitor of LPS-induced TNFα production in human macrophages (FIG. 5). 70% inhibition was observed at 1 µM 24 and overall inhibition reached 90% at 40 µM. Compound 24 exhibited no toxicity or agonist activity in the tested 0.2 to 40 µM range. Curve fitting of the inhibition data in FIG. 5 produced an IC$_{50}$ value of 470 nM. These results were superior to those obtained with compound 4, which had an inhibition range from 3-10 µM and began to show agonist activity at concentrations >10 µM (FIG. 6). Compound 4 was toxic at high concentrations.

The potent inhibition displayed by compound 24 of LPS-induced TNFα production without associated toxicity establishes this compound and those in its class as significant therapeutic and research compounds. These results extend the work of Boons and co-workers with phosphateless Lipid A derivatives by transitioning from disaccharide-based to monosaccharide-based compounds. The IC$_{50}$ inhibition constant of 470 nM for compound 24 is the lowest reported for a monosaccharide compound and its potency in human macrophages significantly improves on the monosaccharide compounds tested in mouse bone-marrow-derived macrophages by Pen et al. While other compounds may have higher potency, the value of the compounds described herein is enhanced by their facile syntheses, which can be readily modified for preparing other derivatives. Additionally, the observation that replacement of the acyl chains in 19 with alkyl chains (24) produced a significantly more potent antagonist with less toxicity indicates that additional modifications can further enhance the activity of the specific compounds described herein. Furthermore, subtle structural changes can have an impact on whether a particular compound displays antagonist or agonist activity. Adjuvants using the compounds described herein may be prepared as described by Deng et al. (*J. Am. Chem. Soc.*, 2008, 130, 5860-5861), Maiti et al. (*Eur. J. Org. Chem.*, 2010, 80-91), and Tang et al. (*Chem. Eur. J.*, 2010, 16, 1319-1325).

Studies described herein provide new Lipid A analogs, and methods for inhibiting and preventing the deleterious effects of endotoxemia. Results of the studies described herein, such as those illustrated in Table 1, will have a far reaching impact on the treatment of patients diagnosed with endotoxemia.

TABLE 1

Compound biological activity in human macrophage cells.

| Compound | TNFα inhibition ($IC_{50}$) | Toxicity | Agonist activity |
|---|---|---|---|
| 10, 12, 13 | None observed | None observed | None observed |
| 11 | 46 μM | >10 μM | None observed |
| 19 | 3 μM | >10 μM | 10-30 μM |
| 24 | 0.5 μM | None observed | None observed |
| 4 | 6 μM | >30 μM | 30-100 μM |

Accordingly, the compounds described herein can be used as antagonists of LPS activity, such as for treating patients diagnosed with endotoxemia. For example, compound 24 is a potent and non-toxic antagonist of lipopolysaccharide (LPS)-induced inflammation in human macrophage cells, including inflammation associated with endotoxemia, septic shock, or Alzheimer's disease. The working concentration of the compounds can be in the low micromolar to sub-micromolar range and the compounds can be effective at blocking cytokine production by LPS (10 ng/mL) in human macrophage cells.

Example 3

Pharmaceutical Dosage Forms

The following formulations illustrate representative pharmaceutical dosage forms that may be used for the therapeutic or prophylactic administration of a compound, a composition of the compound as described herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |

| (viii) Topical Gel 2 | wt. % |
|---|---|
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

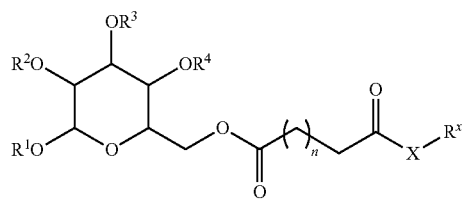

wherein
R$^1$ is (C$_1$-C$_6$)alkyl;
R$^2$ and R$^3$ are each independently (C$_8$-C$_{24}$)alkyl; (C$_8$-C$_{24}$)alkenyl; or (C$_8$-C$_{24}$)alkanoyl;
R$^4$ is H, (C$_1$-C$_6$)alkyl, or aryl;
n is 0-9;
X is O, S, or N;
R$^x$ is an oxygen-linked, sulfur-linked, or nitrogen-linked amino acid that is optionally protected on oxygen or nitrogen with an oxygen or nitrogen protecting group;
wherein any alkyl, alkenyl, alkanoyl or aryl is optionally substituted with one or more hydroxy, oxo, alkyl, alkoxy, alkylcarbonyl, alkylcarbonyloxy, nitro, halo, trifluoromethyl, trifluoromethoxy, cyano, or amino groups;
or a pharmaceutically acceptable salt or solvate thereof.

2. The compound of claim 1 wherein X is oxygen and R$^x$ is oxygen-linked serine, threonine, or tyrosine.

3. The compound of claim 1 wherein X is sulfur and R$^x$ is sulfur-linked cysteine.

4. The compound of claim 2 wherein the amino group of the serine, threonine, or tyrosine is protected with a nitrogen protecting group.

5. The compound of claim 4 wherein the nitrogen protecting group is an acyl, alkyl, or carbamate group.

6. The compound of claim 1 wherein the compound of Formula I is a compound of Formula II:

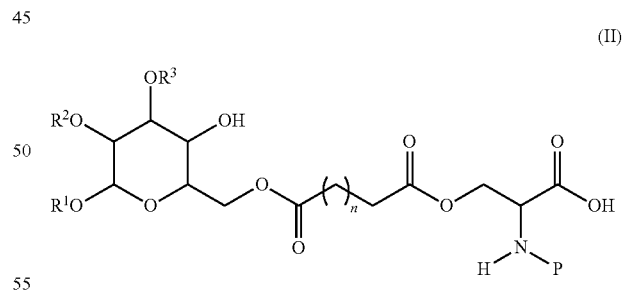

wherein
R$^1$ is (C$_1$-C$_6$)alkyl;
R$^2$ and R$^3$ are each independently (C$_8$-C$_{24}$)alkyl; (C$_8$-C$_{24}$)alkenyl; or (C$_8$-C$_{24}$)alkanoyl;
n is 0, 1, 2, or 3; and
P is a nitrogen protecting group;
or a pharmaceutically acceptable salt or solvate thereof.

7. The compound of claim 6 wherein P is an Fmoc group.

8. The compound of claim 6 wherein the compound of Formula II is a compound of Formula III:

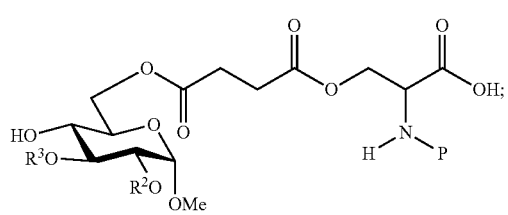

(III)

wherein
R² and R³ are each independently (C₈-C₂₄)alkyl; (C₈-C₂₄)alkenyl; or (C₈-C₂₄)alkanoyl;
and P is a nitrogen protecting group;
or a pharmaceutically acceptable salt or solvate thereof.

9. The compound of claim 1 wherein R² and R³ are (C₁₀-C₁₈)alkyl, (C₁₀-C₁₈)alkenyl, or (C₁₀-C₁₈)alkanoyl groups.

10. The compound of claim 9 wherein R² and R³ are tetradecanoyl groups, tetradecanyl groups, or a combination thereof.

11. The compound of claim 1 wherein the compound is

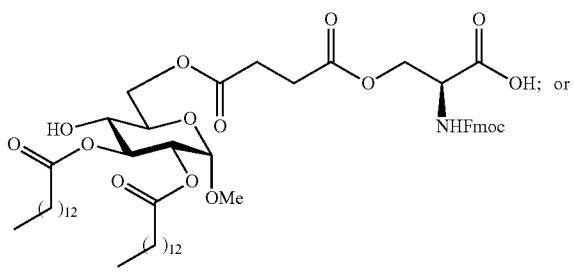

19

; or

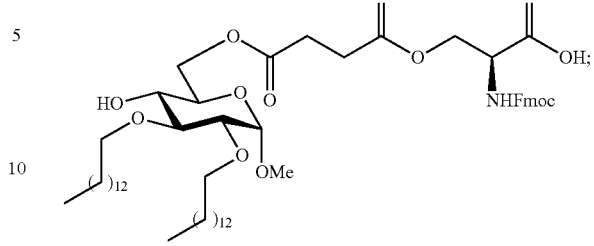

24 or a pharmaceutically acceptable salt thereof.

12. A composition comprising a compound of claim 1 and a pharmaceutical carrier, diluent, or excipient.

13. The composition of claim 12 wherein the composition is formulated for intraperitoneal injection or infusion to a mammal.

14. A composition comprising a compound of claim 11 and a pharmaceutical carrier, diluent, or excipient.

15. The composition of claim 14 wherein the composition is formulated for intraperitoneal injection or infusion to a mammal.

16. A method for treating or inhibiting the deleterious effects of endotoxemia comprising administering to a subject afflicted with endotoxemia an effective amount of a composition of claim 15 wherein the deleterious effects of endotoxemia are thereby treated or inhibited.

17. The method of claim 16 wherein the deleterious effects of endotoxemia are one or more of a reduction in white blood cells, a high respiratory rate, an elevated heart rate, an elevated temperature, or multiple organ failure.

18. A method for blocking or inhibiting a signal transduction pathway in gram-negative bacteria that leads to sepsis comprising administering to a subject afflicted with, or having an increased risk of being afflicted with, sepsis, an effective amount of a composition of claim 15 wherein the signal transduction pathway that leads to sepsis is blocked or inhibited.

19. A method to antagonize LPS signaling in gram-negative bacteria that leads to sepsis comprising administering to a subject afflicted with, or having an increased risk of being afflicted with, sepsis, an effective amount of a composition of claim 12 wherein LPS signaling is antagonized by the administration of the composition.

* * * * *